(12) United States Patent
Cooper

(10) Patent No.: US 10,520,432 B2
(45) Date of Patent: *Dec. 31, 2019

(54) MODULAR ILLUMINATION AND SENSOR CHAMBER

(71) Applicant: Donald Channing Cooper, Boulder, CO (US)

(72) Inventor: Donald Channing Cooper, Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/951,102

(22) Filed: Apr. 11, 2018

(65) Prior Publication Data

US 2018/0299376 A1 Oct. 18, 2018

Related U.S. Application Data

(63) Continuation-in-part of application No. 14/936,966, filed on Nov. 10, 2015, now Pat. No. 9,983,139.

(60) Provisional application No. 62/077,890, filed on Nov. 10, 2014.

(51) Int. Cl.
*G01N 21/47* (2006.01)
*G01N 31/22* (2006.01)
*G01N 33/543* (2006.01)

(52) U.S. Cl.
CPC .......... *G01N 21/474* (2013.01); *G01N 31/22* (2013.01); *G01N 33/543* (2013.01)

(58) Field of Classification Search
CPC .. G01N 21/474; G01N 21/8483; G01N 31/22; G01N 33/543

USPC ........................................................ 422/403
See application file for complete search history.

(56) References Cited

U.S. PATENT DOCUMENTS

| 7,283,245 | B2* | 10/2007 | Xiao ............... G01N 21/253 356/446 |
| 9,329,159 | B2* | 5/2016 | Walicki .............. G01N 21/78 |
| 9,983,139 | B2* | 5/2018 | Cooper .............. G01N 21/78 |
| 2011/0256024 | A1 | 10/2011 | Cole |
| 2012/0270600 | A1 | 4/2012 | Zelson |
| 2012/0282154 | A1 | 11/2012 | Slowey et al. |
| 2014/0078594 | A1 | 3/2014 | Springer |
| 2015/0002950 | A1 | 1/2015 | O'Neill |

* cited by examiner

*Primary Examiner* — Jill A Warden
*Assistant Examiner* — Jacqueline Brazin
(74) *Attorney, Agent, or Firm* — Kenneth Altshuler

(57) ABSTRACT

Embodiments described are generally directed to a test sample apparatus. The test sample apparatus generally comprises a holder base arranged that accommodates a tablet or cell phone. The apparatus has a hood that is placed over a portion of the tablets illuminating touchscreen such that the illuminating touchscreen provides light that can be collected by the hood. There is a chamber integrated with the hood adapted to accommodate a chemically activated test strip. The chemically activated test strip is illuminated when the hood collects light from the illuminating touchscreen. A lens in the hood interposed between the camera and the test strip enables the camera to focus on a portion of the chemically activated test strip when the hood is placed over the portion of the illuminating touchscreen.

19 Claims, 22 Drawing Sheets

MODULAR ILLUMINATION AND SENSOR CHAMBER

CROSS-REFERENCE TO RELATED APPLICATIONS

This application is a Continuation-in-Part and claims priority to and the benefit of U.S. Provisional Patent Application No. 62/077,890 entitled: MODULAR ILLUMINATION AND SENSOR CHAMBER, filed on Nov. 10, 2014, and U.S. patent application Ser. No. 14/936,966 entitled: MODULAR ILLUMINATION AND SENSOR CHAMBER, filed on Nov. 10, 2015 the entire disclosures of which are hereby incorporated by reference.

FIELD OF THE INVENTION

The present invention relates generally to test strip analysis using diffuse light from hand held devices, and more particularly to tools and methods used outside a laboratory for biological sampling.

BACKGROUND

Over recent years, biological sampling and testing in remote places is being seen as an important step in disease prevention and care. Today, most testing for disease or hazardous materials is done in a lab. These labs a located in cities or places that can accommodate first world equipment. Unfortunately, most of these labs are far from places where people are effected by hazardous materials and/or disease. Given advances in computing power of personal computers and hand held devices, laboratory services and test strip analysis may expand beyond central locations.

It is to improvements in test strip analysis using hand held devices that embodiments of the present invention are directed.

SUMMARY

Embodiments of the present invention are directed to test strip analysis using diffuse light from hand held devices with general accessibility to tools and methods used outside a laboratory for biological sampling.

One embodiment described herein contemplates a modular specimen illumination and positioning chamber system that attaches to mobile devices for the purposes of improving data acquisition resulting from imaging organic and nonorganic test specimens. The removable chamber is affixed directly over a front-facing camera and partially over an illuminated display screen in a consumer tablet or touchscreen cell phone, for example. The chamber gathers light from the illuminated display screen to provide indirect diffuse lighting to a specimen test strip. The color of the screen illumination region immediately under the chamber and the brightness of the screen may be adjusted programmatically using software algorithms to enhance specimen image acquisition. The chamber is capable of operating under a variety of mobile device orientations and is robust to physical disruption from dropping.

Embodiments can generally include modular specimen positioning with the use of an analysis chamber. One embodiment contemplates a mobile device at least partially contained in a base module having a protective case. The base module possessing an integrated removable lens holder. The base module adapted to accommodate a top stage module containing a window and removable specimen stage that fits on the base module in an adjustable manner in order to position the specimen in front of the front-facing camera. A portion of the base module chamber covers the display screen of the mobile device in an adjustable manner to gather light from the screen to optimally illuminate the chamber with indirect diffuse light. One embodiment contemplates the inside of the base module of the chamber being reflective to increase the luminance in the chamber. The walls of either the base or the stage module may be of varying opacities from translucent to opaque depending on the type of specimen and the type of imaging. The mobile device attached base module and lens holder may be moved from covering a portion of the display screen by sliding away from the display screen or pivoting on a hinge or axel from the display screen when loading the specimen, so that the camera can be used for non-magnified imaging or when the full touch screen is needed for user interaction.

The top stage module can be customized to accommodate the specimen. Embodiments contemplate the top stage module being removable and adjustable to accommodate X, Y and Z spatial positioning for securing a variety of specimen form factors and materials including wet and dry specimens for the purpose of image acquisition and analysis of the specimens.

Ancillary modules are envisioned to monitor specimen position in the chamber, changes in color and size of the specimen, environmental variables (such as temperature, humidity and wind or fluid velocity and volume), specimen source identification. Optional ancillary modules are further envisioned being capable of monitoring during sampling or imaging. Further modules may be employed for data storage security, such as for subsequent analysis.

DETAILED DESCRIPTION

Initially, the present disclosure is by way of example only, not by limitation. Thus, although the instrumentalities described herein are for the convenience of explanation, shown and described with respect to exemplary embodiments, it will be appreciated that the principles herein may be applied equally in other types of situations involving biological sampling consistent with spirit and scope of the present invention.

Figure 1:
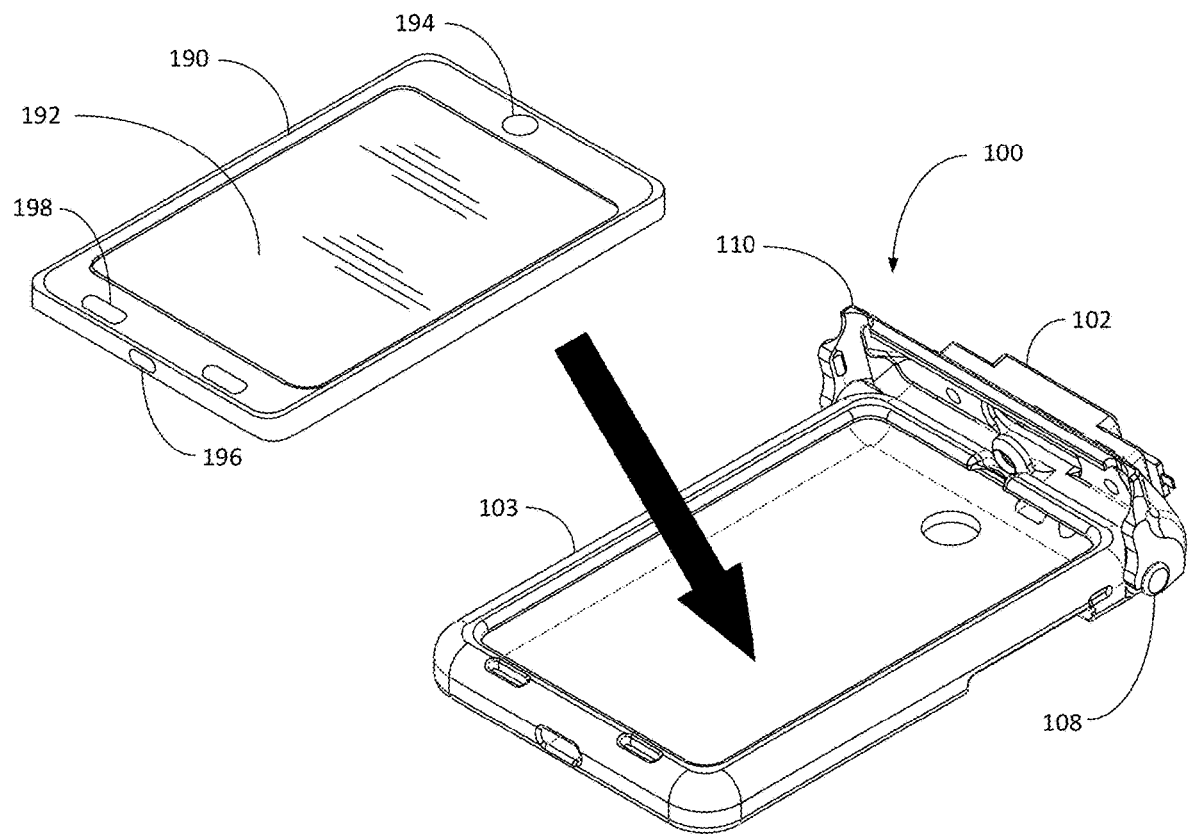
FIG. 1 illustratively depicts an embodiment of a handheld tablet or phone to be placed inside protective case embodiment consistent with embodiments of the present invention.

To illustrate an exemplary environment in which preferred embodiments of the present invention can be practiced, FIG. 1 depicts an embodiment of a cell phone/tablet 190 that is to be placed inside of a protective case 100, or more specifically the protective case base 103. Certain embodiments contemplate the protective case base 103 essentially conforming to all sides of the cell phone/tablet 190 while other embodiments contemplate the protective case base conforming to only a portion of the cell phone/tablet 190. The cell phone 190 is simply an embodiment of a tablet or other handheld electronic device that could likewise be used within the scope and spirit of the present invention. As illustratively shown, the cell phone/tablet 190 possesses a screen 192, preferably a touchscreen, a camera 194, speakers 198, and power inlet 196, etc. The protective case 100 possesses a hood 110 that is adapted to be pivoted to over a portion of the cell phone/tablet 190. The arrow indicates where the cell phone/tablet 190 is placed inside of the protective case 100.

Consumer electronic mobile devices, such as tablets or phones 190, capable of wireless (Wi-Fi or cellular network) data transmission have computer processing capability and user interface operating systems. Most have a fixed-focal-length camera 194 that are positioned above the illuminated display screen 192, called a front-facing camera. The display screens 192 are typically touch screens that enable users to interact with the operating system via touching the screen when 92. The screens are color displays consisting of Red, Green Blue, Cyan or Magenta colored pixels capable producing any color combination. In addition, the illumination of the screen display can be adjusted in brightness from 0 to 100% of the device output.

Figure 2A:
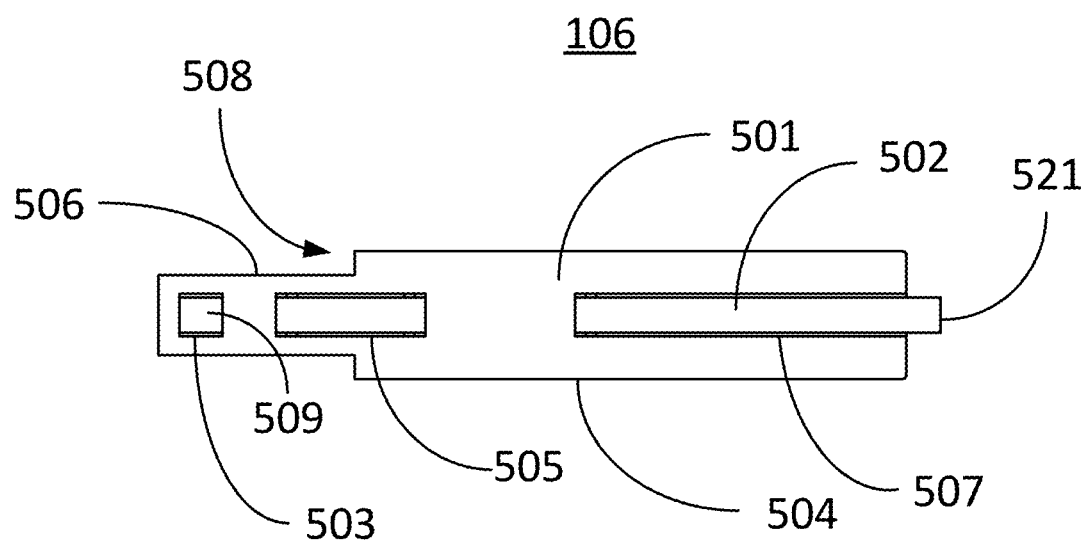
FIGS. 2A-2C depicts illustrations of a strip holder with a test strip consistent with embodiments of the present invention.
Figure 2B:
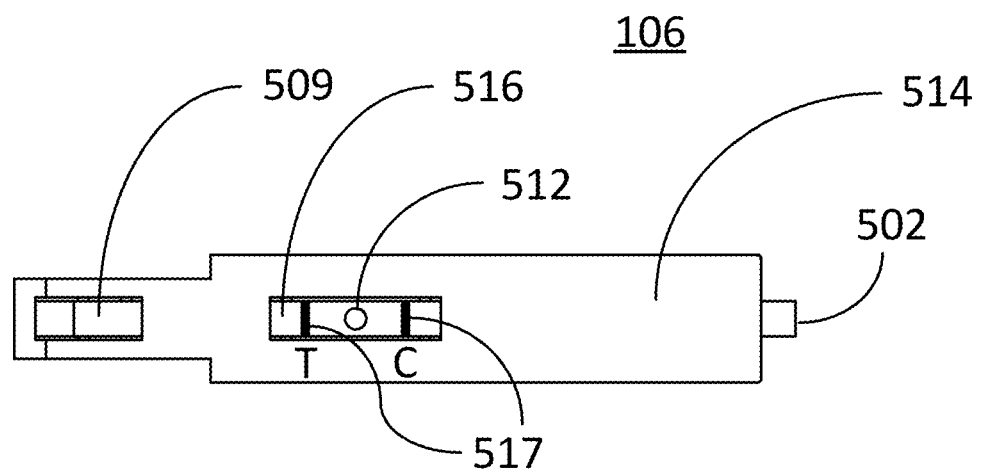

With reference to FIGS. 2A and 2B, depicted therein are illustrations of a customized strip holder 106 accommodating a test strip 502. FIG. 2A illustratively shows the top surface 501 of the customized strip holder 106 and FIG. 2B illustratively shows the bottom surface 514 of the customized strip holder 106. The present test strip 502 embodiment is a lateral flow test strip 502. Certain embodiments contemplate the test strip 502 being a chemically activated test strip, that is when molecules of a specific substance are migrated through the test strip 502 they react with Test and Control lines to indicate the presence of the molecules. From the perspective of the top surface 501, the lateral flow test strip 502 is exposed in three windows 503, 505, and 507. The test strip 502 comprises three elements of interest: 1) the test pad 509, which is an absorbent material, 2) test and control lines 517, which are used to reveal the outcome of a biological test, and 3) the holding portion 521. When in operation, the absorbent pad 509 is dipped into a test solution, such as a biological solution (e.g., blood, saliva, sweat or any other biological fluid to be extracted from an animal or extracted from grain or plant material with a solvent). The test solution absorbed by the absorbent pad 509 migrates to the testing control region 505 along with antibodies or antigens previously embedded in the test strip 502. Certain embodiments contemplate a test strip that is constructed with nitrocellulose material membrane between 503 and 505 that easily carries the naturally aqueous solution by way of capillary action. The aqueous solution carries the antibodies along the test strip 502 to the imaging window 516, which reveals the test area that provides a visual signal on stripes/lines "T" (Test) and "C" (Control) 517 within imaging window 516. The center of the imaging window 516 is illustratively shown by the circle 512. The center of the imaging window referenced by the circle 512 is the location where the cell phone/tablet 190 camera 194 centers on the test strip 502 to evaluate the stripes "T" and "C" 517.

The "T" and "C" stripes 517 are not originally visible (or present) until the test solution is absorbed and transferred to the testing control region 505. More specifically, the antibodies are conjugated to some tag, such as colloidal gold, wherein the antibodies bind to the binding site "T" on the membrane 502. The lines "T" and "C" 517 become gradually darker depending on (directly related to) the particular analyte that is being tested. The control line "C" is a standard line reference where the antibodies conjugate. The test line "T" has either a) a competitive interaction with the test analyte and the binding site, "T", such that when there is more analyte the test line "T" gets darker or b) it is configured in a sandwich assay where the signal becomes darker with an increasing amount of analyte. A rapid diagnostic test strip, such as a pregnancy test strip, is an example of a standard test strip 502. Neogen Corporation of Lansing, Michigan can provide a test strip to test for mycotoxins, which can be aptly used, for example, in the present embodiment. In one example, a ratio metric and can be used to quantify the intensity of the test signal "T" relative the control signal "C", which can be calibrated to a standard curve having known signal intensities, to determine the concentration of a particular analyte in solution.

With continued reference to the structure of customized strip holder 106, the is a shoulder 508 that acts as a "stop" to position the customized holder 106 and test strip 502 appropriately in the top chamber 102 so that the test lines "T" and "C" 517 are centered over the tablet camera 194.

Figure 2C:
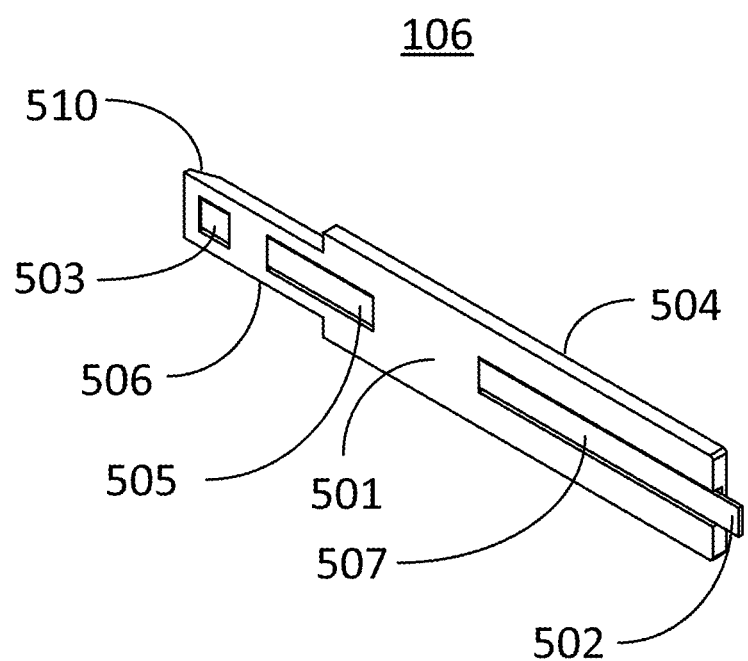

FIG. 2C illustratively depicts a perspective drawing of the customized strip holder 106 with the top surface 501 revealed. Note that the customized strip holder 106 possesses a leading ramp 510 that facilitates an easy insertion of the customized strip holder 106 into the top chamber 102. The customized strip holder 106 and test strip 502 allow for a user to start developing the test strip 502 while holding the customized strip holder 106 prior to insertion into the top chamber 102.

Figure 3A:
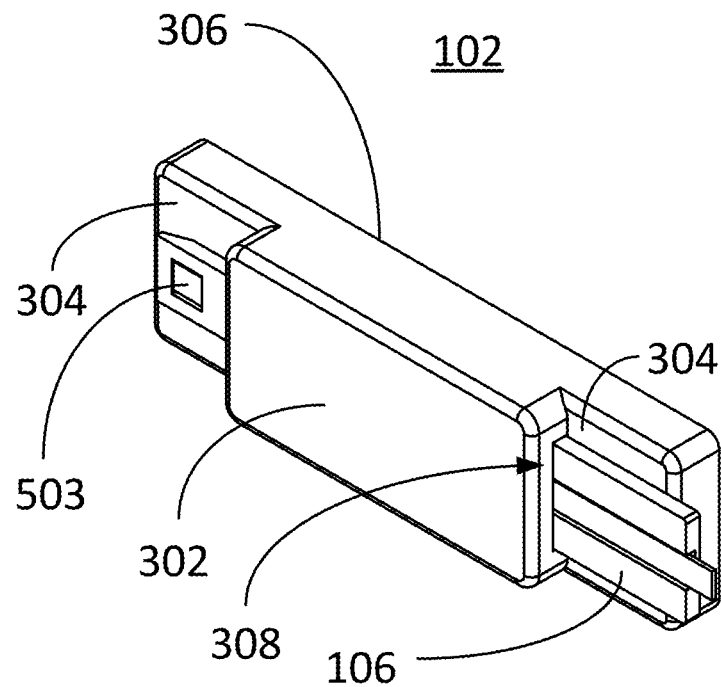
FIGS. 3A-3D illustratively depict an embodiment of a top chamber consistent with embodiments of the present invention.
Figure 3B:
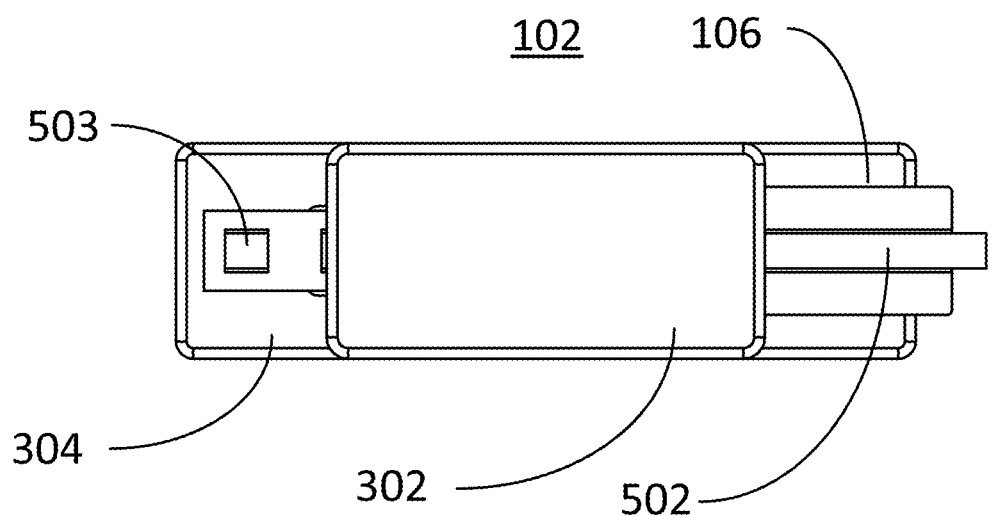
Figure 3C:
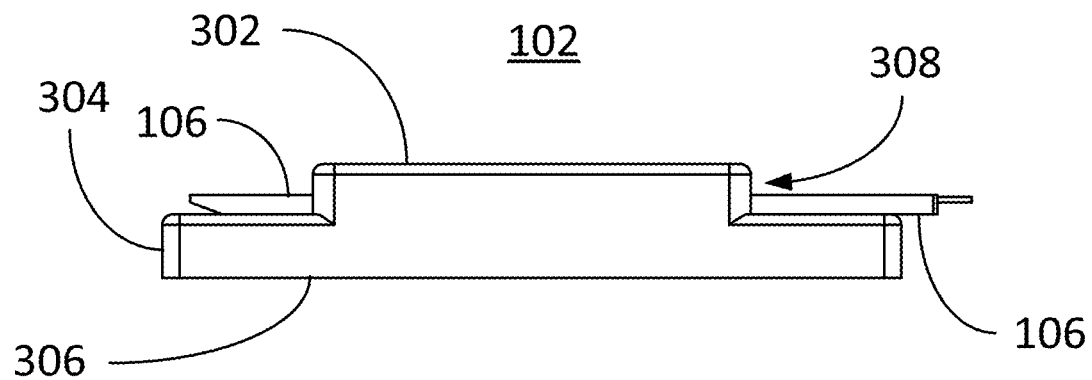

FIGS. 3A-3D illustratively depict an embodiment of a top chamber 102 adapted to affix to the hood 110, the top chamber 102 consistent with embodiments of the present invention. Embodiments contemplate the top chamber 102 accommodating any number of standard test strips and certain embodiments contemplate other standards strip holders, that may be different from the strip holder 106 depicted in FIG. 2A, for example. FIG. 3A depicts a perspective view of the top chamber 102 with the customized strip holder 106 accommodating a test strip 502. The top chamber 102 position in view of the top surface 302 depicts a pair of steps 304 that provides access to the front window 503 and easy access to the insertion location 308. Other embodiments of the top chamber 102 envision optional geometries to provide access to the front window 503 and insertion location 308, consistent with embodiments of the present invention. The customized strip holder 106 is disposed in the top chamber 102 by way of a strip holder insertion location (opening) 308. FIG. 3B depicts the top view of the top chamber 102. Again, as illustratively depicted, the top surface 302 steps down into a lower surface 304 whereby the customized strip holder 106 provides visibility to the front window 503 and access to insert and remove the customized strip holder 106 at the insertion location 308. FIG. 3C illustratively depicts a side view of the top chamber 102. As shown, the customized strip holder 106 is held in place in the top chamber 102. The customized strip holder 106 is inserted through the insertion location 308 from the right side of the top chamber 102 to the left side of the top chamber 102. Also shown, is the bottom surface 306 of the top chamber 102, which is affixed to the hood 110.

Figure 3D:
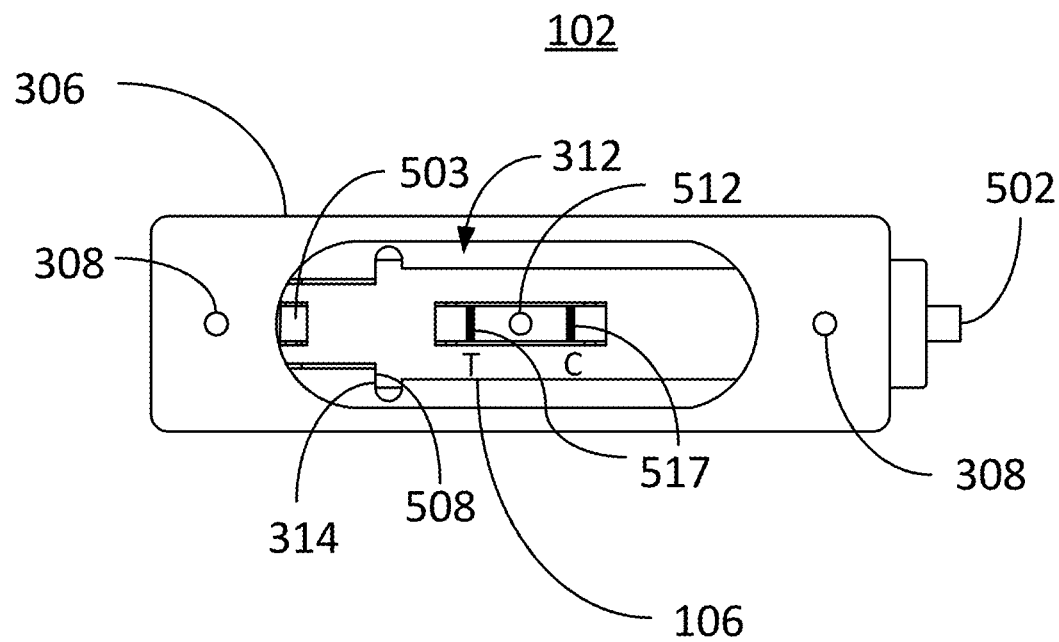

With reference to FIG. 3D, shown therein is the bottom surface 306 of the top chamber 102 consistent with embodiments of the present invention. The bottom surface 306 of the top chamber 102 possesses a pair of holes 308 (potentially screw holes) that can affix the top chamber 102 to the hood 110. Embodiments contemplate other elements of fixing the top chamber 102 to the hood 110, such as magnets, screws, pins, adhesive, latches, etc. As shown here, the customized strip holder 106 is exposed through an opening 312 extending through the bottom surface 306 of the top chamber 102. In this way, the test strip 502 is exposed to the camera 194 in the tablet 190 via the opening 312 in order to be analyzed by the camera 194. Also, shown is the shoulder 508 butting up against the mating surface 314 in the top chamber 102 to position the center of the imaging window 516 and the test strip 502 (the circle 512) with the focal point of the camera 194. Embodiments contemplate the opening 512 and the testing control region 505 positioned in a different location to be aligned with one or more cameras if located on the front of a tablet 190 in a different locations, such as on the side or not in the midpoint between the two sides of the tablet 190.

Figure 4A:
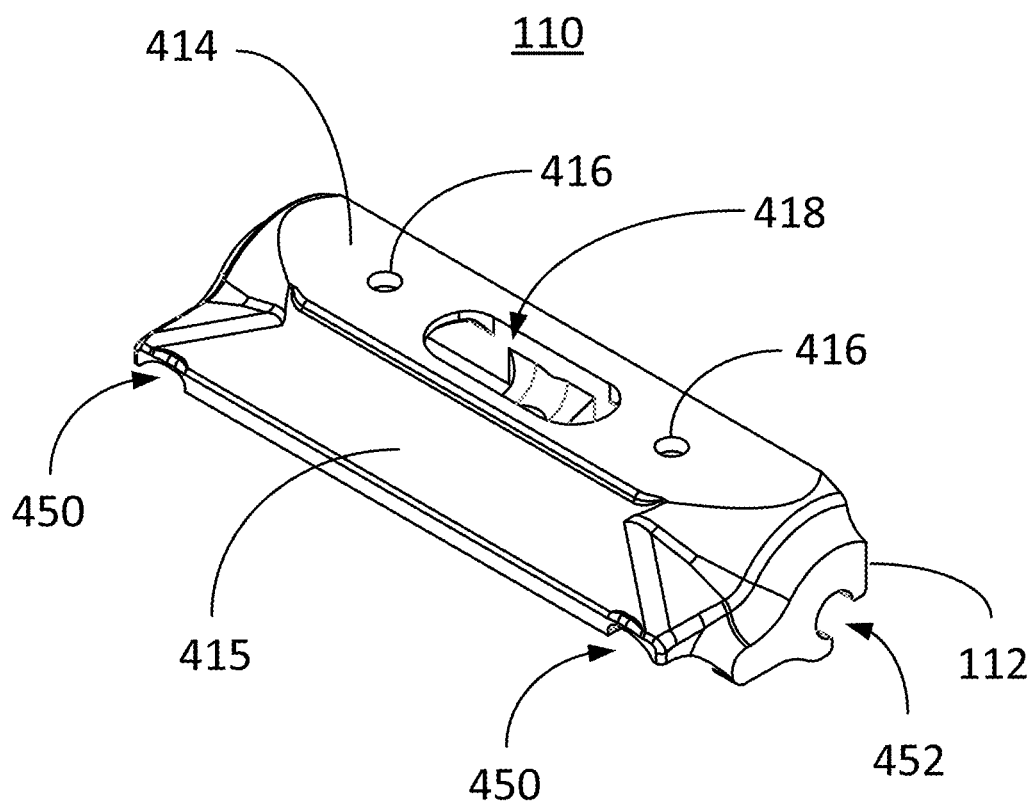
FIGS. 4A-4C, depict illustrations of a flip hood embodiment is depicted consistent with embodiments of the present invention.

FIG. 4A depicts a perspective illustration of a flip hood embodiment consistent with embodiments of the present invention. As shown, the flip hood 110 possesses a top surface 414 without the top chamber 102 mounted thereon. There are two holes 416 that align with the two holes 308 from the top chamber 102. Accordingly, the top chamber 102 can be affixed to the flip hood 110 via magnets, screws, adhesive, pins, latches, and the like without departing from the scope and spirit of the present invention. The top surface 414 of the flip hood 110 possesses a flip hood opening 418 through which light from the screen 192 can illuminate the test strip 502 and the camera 194 can freely image the illuminated test strip 502 via the opening 312 in the top chamber 102. The flip hood 110 possesses two hinge points 452 on the sides 112 that cooperate with two posts 108 protruding from the protective case base 103. The two hinge points 452 enable the flip hood 110 to rotate away from the screen 192 so that a user of the tablet 190 can enter in data or use the screen 192 without obstruction of the hood covering part of the screen 192. Furthermore, rotating the flip hood 110 away from the screen 192 facilitates disposing or removing the tablet 190 from the protective case base 130. The flip hood 110 further possesses a flip hood cover 415 that slopes down from the top surface 414 and is adapted to collect light emitted by the screen 192 from the tablet 190. Also depicted, are two flip hood notches 450 that mate with protrusions 160 on the protective case base 103 to hold the flip hood 110 in a down position when examining a test strip 502. Optional embodiments contemplate the flip hood 110 being held down in a held or latched in position with the help of magnets or two rubber foot protuberances on the back, bottom surface of the flip hood which extend beyond the case back surface to allow the device's weight to rotate the hood to keep it closed, for example prior to illuminating the sample and taking a picture. Other latching embodiments can include locking features, snapping features, Velcro, and the like within the scope and spirit of the present invention.

Figure 4B:
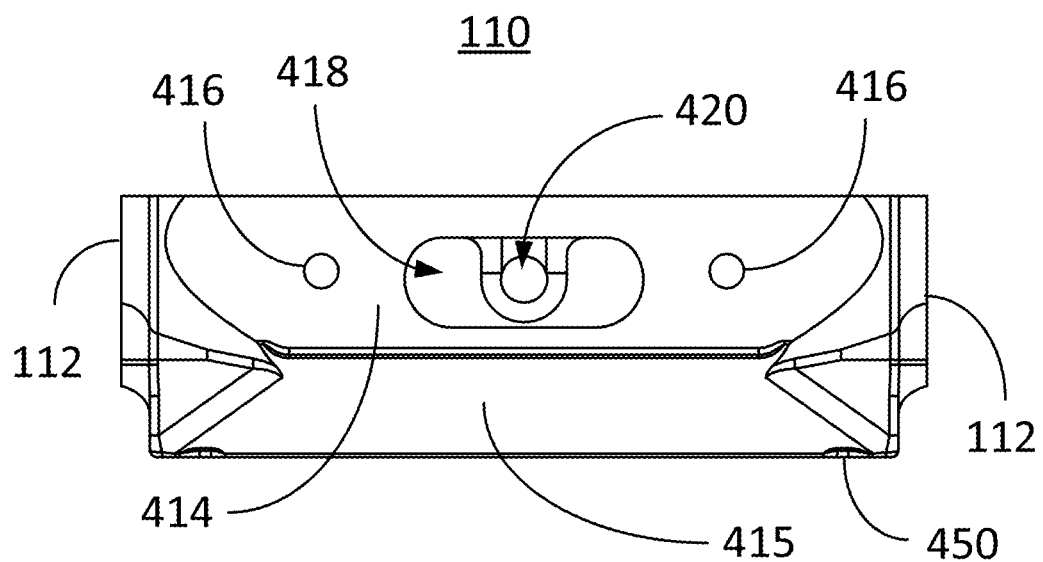

FIG. 4B depicts a top view of the flip hood 110 consistent with embodiments of the present invention. The two holes 416 are located in the top surface 414 as previously discussed. The flip hood opening 418 reveals a lens 420 that is located directly above the camera 194 associated with the tablet 190 to bring the center point 512 of the imaging window 516 into focus. The lens 420 is preferably a convex lens, but can be a plurality of different kinds of lenses to produce different levels of magnification and focus within the scope and spirit of the present invention. Some lenses 420 may have different focal lengths and magnifications and may be spherical, semispherical, planar, concave or convex in shape and may be made from glass, epoxy, polyacrylamide, plastic, liquid or other translucent or tinted materials. The lens 420 may be disposable convex planar and made of aqueous liquid containing translucent or tinted polyacrylamide to provide magnification at different powers from 2× to 40× depending on the size of the semispherical disposable lens and may be tinted to serve as a filter to allow specific wavelengths of light to pass 420. For reference, the flip hood notches 450 are shown on the flip hood cover 415.

Figure 4C:
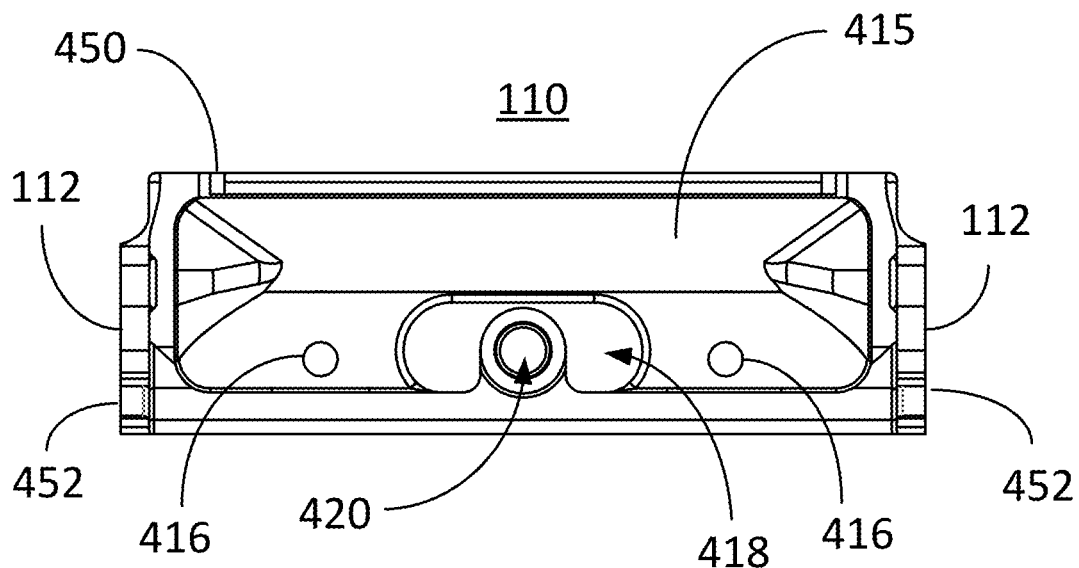

FIG. 4C depicts an underneath view of the flip hood 110 consistent with embodiments of the present invention. As is illustrative of shown, the flip hood opening 418 shows the lens 420 located in the middle of the flip hood opening 418. Other embodiments contemplate the lens 420 capable of being adjusted to the left or to the right in the flip hood opening 418 to adjust in alignment with the camera 194 in the tablet 190. Optionally, other embodiments contemplate the lens 420 capable of being removed altogether. From the underneath perspective, the flip hood 110 shows the attachment holes 416, the sides 112, the two hinge points 452, the two flip hood notches 450, and the flip hood cover 415. As discussed earlier, the flip hood cover 415 collects light emitted from the screen 192 of the tablet 190 to expose the test strip through the flip hood opening 418.

Figure 5A:
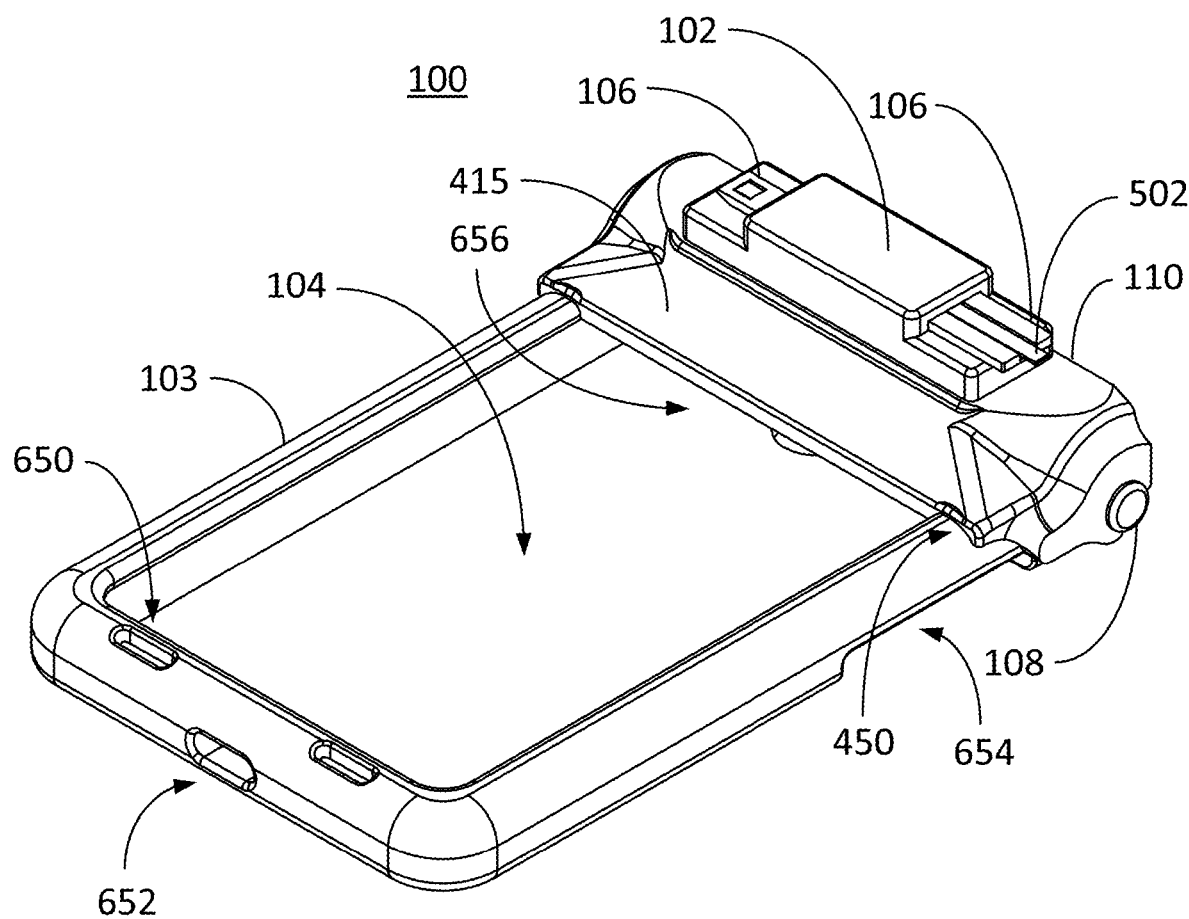
FIGS. 5A-5B illustratively depicts an embodiment of the protective case in more detail in accordance with embodiments of the present invention.

FIG. 5A illustratively depicts an embodiment of the protective case 100 in more detail in accordance with embodiments of the present invention. In the present drawing, there is no tablet 190 present. In the present view, the flip hood 110 is latched down in the closed position, which is spaced apart from where the screen 192 of the tablet 190 would reside if present. The flip hood 110 (a light collection chamber) is spaced a distance apart 656 from the screen 192 in order to a) collect light from the screen 192 and b) provide adequate distance between the customized strip holder 106, and more specifically the test strip 502. Preferably, the flip hood 110 is spaced at distance apart 656 from the screen 192 between 1 mm and 6 mm, though other embodiments envision different dimensions. The protective case 100 possesses a protective case base 103, which in certain embodiments contemplate being a rubber bumper or some other kind of bumper that allows for deflection to protect the tablet 190. The protective case base 103, in one embodiment, wraps around the tablet 190 holding it snugly in place so that the tablet 190 is constrained and is protected. The protective case 100 can further possess speaker holes 650 and a hole for power 652. One skilled in the art will appreciate that the speaker holes 650 and the power hole 652 may be located in different places in the protective case base 103 in order to accommodate those structures in the tablet 190. Other cutaways, such as the cutaway 654 are envisioned to support other buttons on the tablet 190. Embodiments of the elements found in the protective case 100, though not limited by the following material options, may be made from rubber, silicone, wood, metal, glass, plastic, polyurethane, vinyl, PLA, paper, ABS and other epoxy-based or malleable materials, just to provide some examples.

Figure 5B:
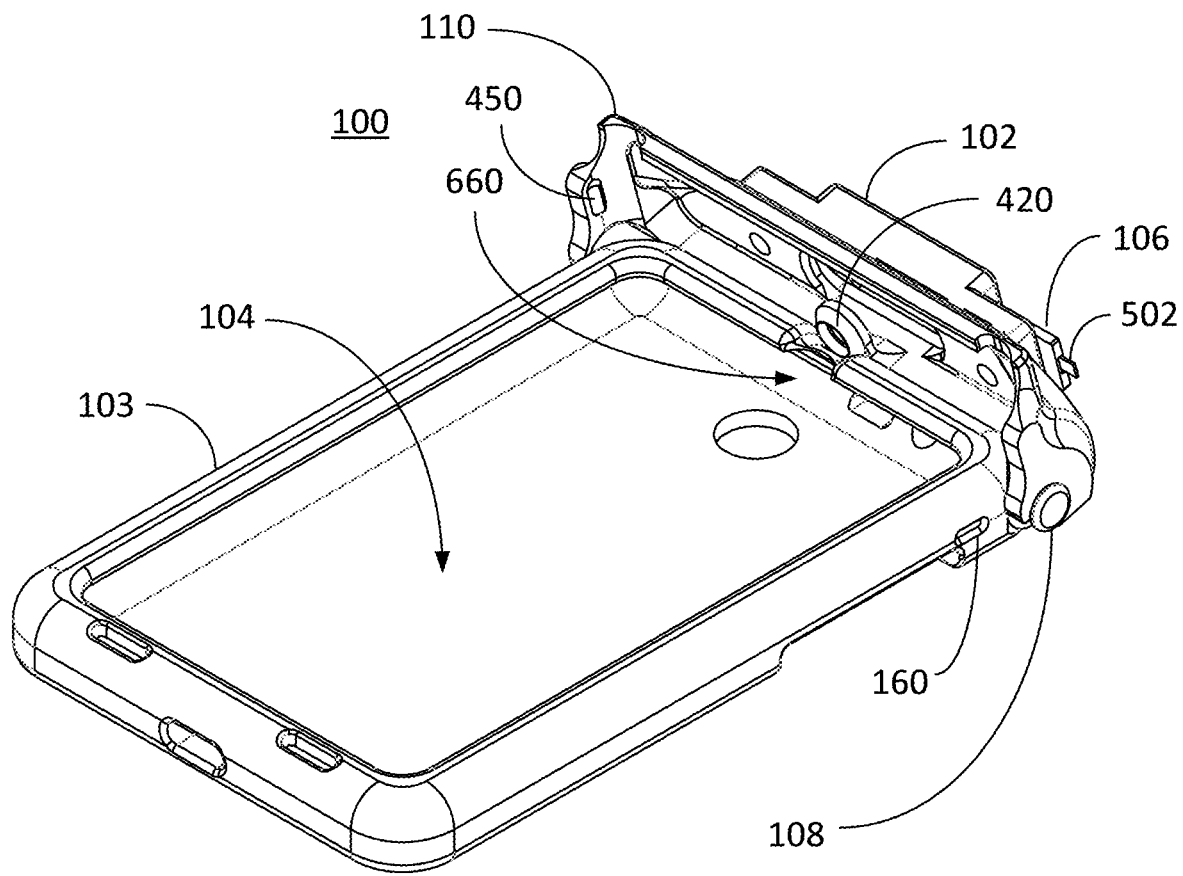

FIG. 5B illustratively depicts an embodiment of the protective case 100 with the flip hood 110 pivoted in an open position to allow for insertion of a tablet 190 or facilitate the use of a touchscreen 192 associated with the tablet 190. In the present embodiment, the side of the protective case base 103 possesses protrusions 160 that mate with the flip hood notches 450 to hold (lock) the flip hood 110 in a down position (in place) when examining a test strip 502. The protective case 100 also possesses a lens cutaway 660 in order to accommodate the lens 420 (and lens structure) when the flip hood 110 is moved between an opening closed position.

Certain embodiments contemplate the flip hood 110 to be further capable of gathering light from the display screen 192 by its physical placement over the screen 192 and redirecting the light to illuminate the specimen 502. This may be aided by the use of highly reflective coating of the interior walls of the base module or by placing mirrors in the chamber 102 and/or the flip hood 110 to redirect light from the display screen to the specimen 502 or from the specimen 502 to the camera lens 194. The display screen illumination may be adjusted to increase or decrease the luminance or wavelength color of light within the chamber 102 to enhance the illumination of the test strip 502 for image acquisition (perhaps ultraviolet or infrared). Certain embodiments contemplate using various wavelengths of light generated by the touchscreen 192, such as ultraviolet, to cause reaction or develop the chemically activated test strip 502 when introduced to a test sample Some embodiments contemplate a filter, prism or pinhole integrated into the lens holder module or, optionally, exist as a separate module for allowing certain wavelengths of light to pass from the specimen to the camera lens. Some embodiments contemplate the walls of the chamber 102 and or flip hood 110 being translucent to allow trans illumination or oblique lighting of the test strip 502 or it may be opaque to shield from ambient light sources depending on the type of test strip 502 and use case.

It is contemplated that the display screen 192 may be adjusted programmatically to increase or decrease the light emitted from it in order to modulate the lighting of the specimen/test strip 502 in the chamber 102. Other embodiments contemplate the display screen 192 being adjustable, to adjust the color of light emanating from the screen used to illuminate the specimen/test strip 502. Certain other embodiments contemplate the tablet or cell phone 190 connecting to a specimen imaging trigger module that may be powered by the tablet or phone 190 via a power port 196, or audio headphone port and the like, to provide an electrical contact with the specimen material of the test strip 502 sensing voltage signals indicating initiation or termination of imaging. This can be used to trigger the camera 194 and/or provide other actions of the tablet or phone 190, such as initiation of imaging, timing, illumination, or analysis of the specimen via software programs/modules. The software applications stored in non-transitory memory in the tablet 190, or elsewhere, can be accessed by the computer system processors in the tablet or elsewhere.

Certain other embodiments contemplate the flip hood 110 or elements associated with the flip hood 110 being adjustable in order to provide precise fixed positioning of the test sample 502 over the camera 194 and illumination screen 192. Certain adjustable mechanism such as finger screws, for example, could adjust the flip hood 110 and associated elements in the X, Y, Z directions.

Figure 6A:
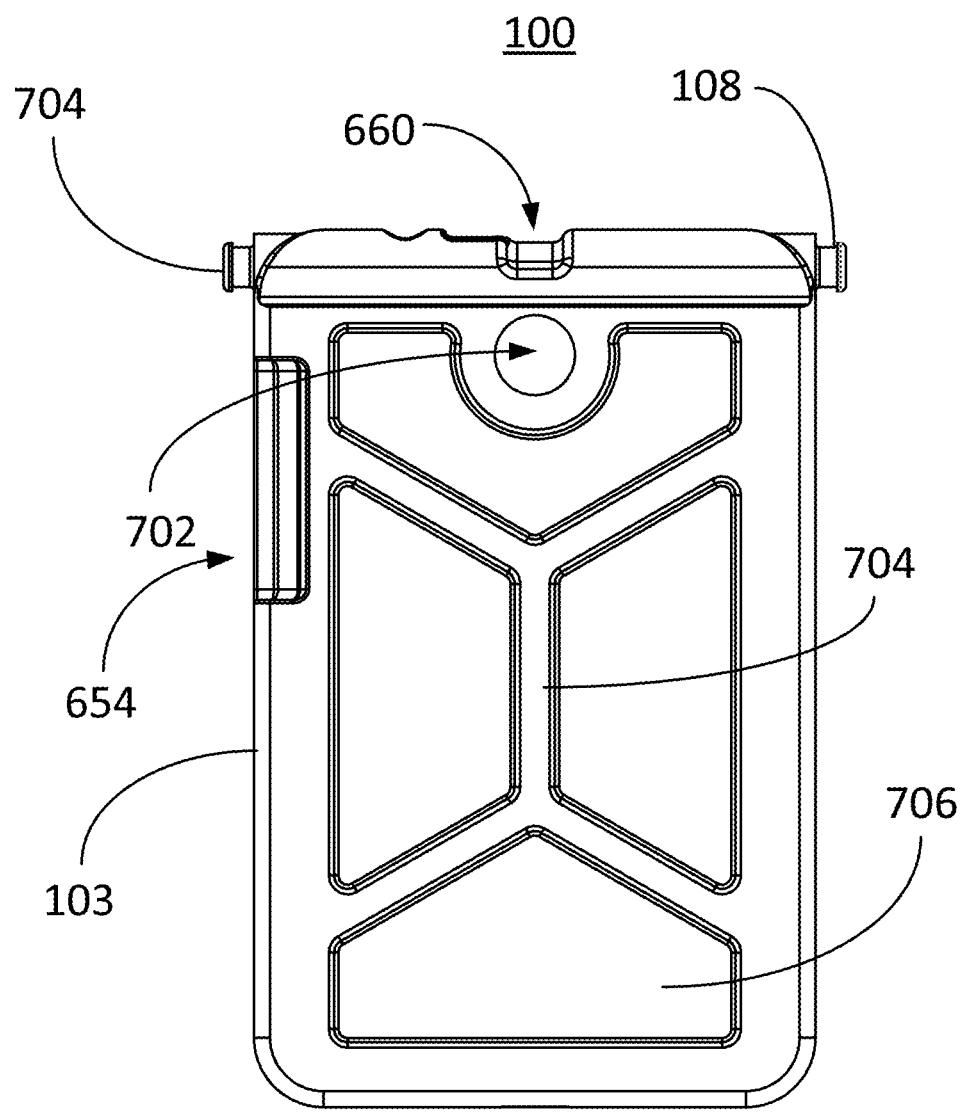
FIG. 6A-6C illustratively depict an embodiment of the protective case consistent with embodiments of the present invention.

FIG. 6A illustratively depicts an embodiment of the protective case 100 as viewed from the bottom. The protective case base 103 possesses a protective case bottom 706 that in this configuration possesses a raised rubber grip 704. The cutaway 654 as described in conjunction with FIG. 5A is shown here providing access to buttons on the tablet 190. Also depicted, is a protective case base reverse side camera opening 702 that provides access to a camera (not shown) on the reverse side of the tablet 190. Also shown, is the lens cutaway 660 and the two posts 108 protruding from the protective case base 103. In this embodiment, each post 108 possesses a rubber ear 704 that is adapted to deflect and retain the flip hood 110 when cooperating with the hinge points 452 on the sides 112. Other embodiments contemplate the posts 108 extending far enough from the protective case base 103 to facilitate a strap (not shown) looping around the posts 108.

Figure 6B:
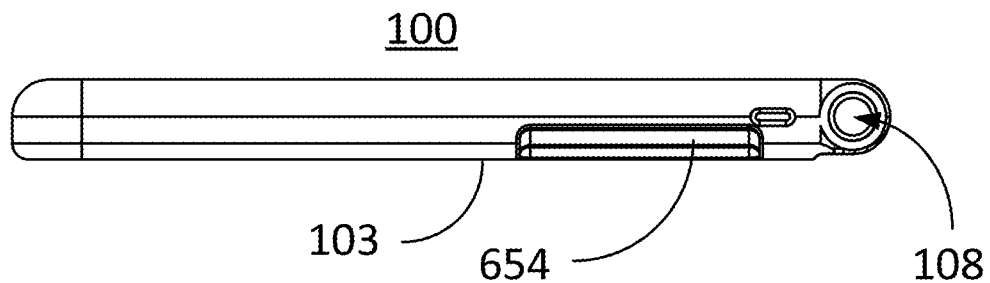

FIG. 6B illustratively depicts the embodiment of the protective case 100 as viewed from the side. As depicted, the protective case base 103 is just thick enough to accommodate the tablet 190, such that the tablet 190 is essentially contained therein and protected. For reference, note the cutaway 654 as described in conjunction with FIG. 5A and one of the posts 108.

Figure 6C:
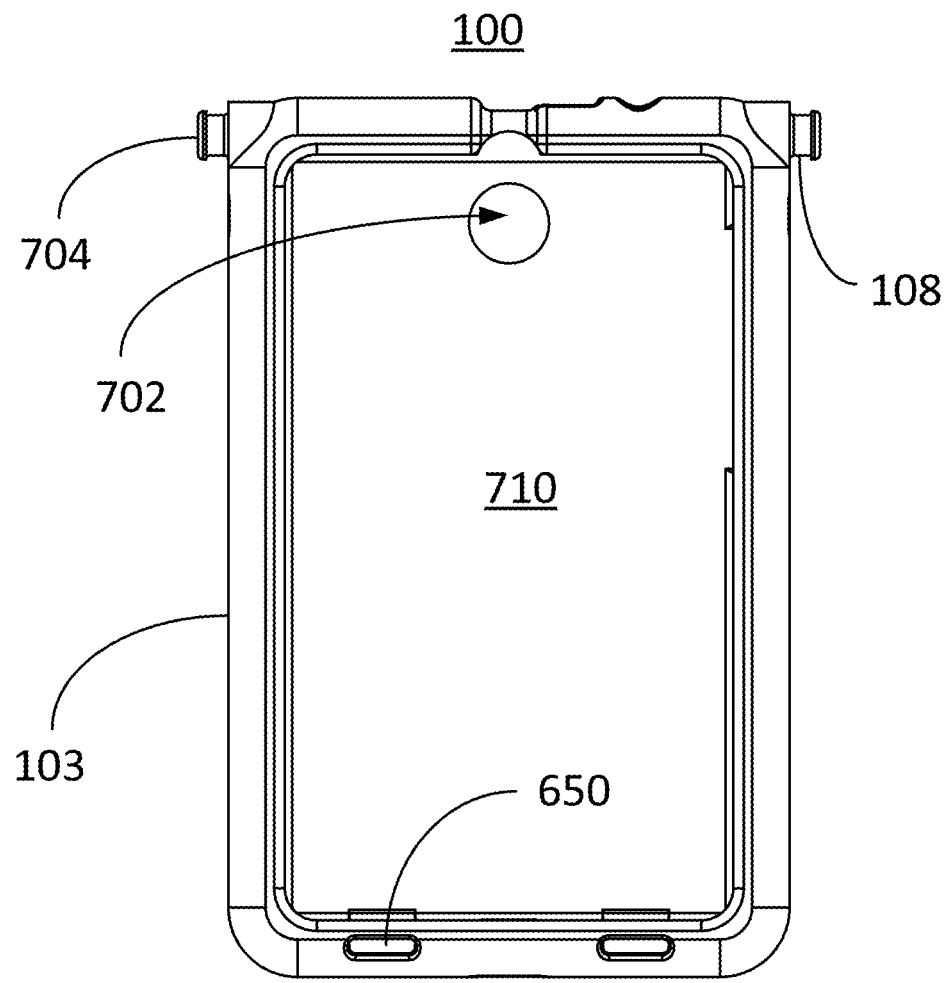

FIG. 6C illustratively depicts the embodiment of the protective case 100 as viewed from the top down. For reference, the protective case base reverse side camera opening 702 is shown penetrating the interior protective case base portion 710. Also, the two posts 108 are shown protruding from the protective case base 103 along with the rubber ears 704 on each post's 108 distal end.

The figures described above are illustrative examples of a protective case 100 and system used with consumer-based mobile electronics for quantitative imaging acquisition and analysis that are solutions to deficiencies in the present state of the art. One of the problems with the present state of the art when evaluating test strips 502 with a light source, typically an LED (Light Emitting Diode) light source, is the variability and quality of the LED "Flash" luminance intensity between devices providing the light. The LED "flash"

operates in a binary on or off mode. There is no software programmatic method of adjusting the output luminance in a continuous manner. In addition, the LED is a high intensity point-source of light, and when imaging objects within a few centimeters of the camera lens and LED light-source artifacts, such as reflection, glare and shadows may be introduced. These artifacts make it difficult to perform quantitative high magnification (>2x) optical imaging of biological samples or "wet/moist" objects on highly reflective surfaces, such as aqueous-sample-treated white nitrocellulose immunotests or glass microscope slides. In addition to the artifacts associated with LED illumination coupled with use of the rear-facing camera (the camera opposite to the touchscreen display 192), the autofocus, ISO, color correction and automatic white balance adjustments that are built in features of many mobile device hardware operating systems (e.g. Windows, Android and iOS) are not uniform in their performance especially for high magnification imaging, which results in variability in the images and makes it difficult for quantification with reliability between devices.

Specimen sampling and analysis of biological fluids and tissues are discovered, via developing this device, to be prone to errors derived from improper sampling procedures, cross-contamination, errors in subject or sample identification, inconsistent methods across individuals or test devices, improper calibration to standards, measurement errors, expired reagents and supplies, improper handling and cold chain management of samples or reagents, lost or corrupted data, fragile test equipment, and intentional data falsification.

Embodiments contemplate the protective case 100 and flip hood 110 (of FIG. 1) providing a cross-platform rugged modular specimen imaging and analysis chamber 102 that are able to work with a variety of mobile devices in order to eliminate variability associated with specimen positioning, illumination, temporal changes in the color or shape of the specimen during testing, specimen source identification and tracking, and environmental fluctuations during testing, and high-risk data storage.

The modular illumination chamber 102 uses a front-facing camera 194 and the illuminated display 192 as an indirect and diffuse light-source from a tablet or cell phone 190. There are several advantages of using the front-facing camera 194 positioned directly above the illuminated display screen 192. Typically, a tablet or cell phone 190 has a fixed focal length camera so there is no automatic autofocus mechanism as a source of variability. In addition, the display luminance and color wavelength on most displays 192 of mobile devices 190 is continuously adjustable from 0 to 100% brightness and from 380 nm (Blue) to 650 nm (Red) wavelengths. Indirect lighting from the display screen 192 into the hood 110 and the illumination chamber 102 provides diffuse, polarized LCD illumination of the specimen 502, which eliminates glare and artifacts associated with point sources of light and with magnified imaging of objects with complex shape (e.g. conical tubes) and/or reflective or wet surfaces.

The ports of audio or micro USB inputs in tablets or cell phones 190 and may be used to collect data before, during or after image acquisition in order to improve specimen positioning, identification, handling, sampling and data storage.

Certain embodiments contemplate instructions being interpreted by the tablet or cell phone 190 via the test sample, such as, information embedded in barcodes, text, shapes, colors, QR codes, or any other reliable identifiable features associated with the specimen for purposes of triggering image acquisition, color and intensity of the illumination screen 192, storage of information to the tablet, real-time digital image analysis, object recognition algorithms, feature detection, background subtraction, filtering methods, contrast enhancements, pattern recognition and other computer vision techniques to assess specimens spatial, spectral and temporal imaging characteristics, for example. Real-time image acquisition and analysis can benefit from the combined use of the illumination specimen positioning modules, display screen illumination and color determination, mobile device user input and software algorithms running on the mobile device to perform/execute the computational algorithms.

With respect to the test lines "T" and "C" 517, certain embodiments contemplate analyzing test lines "T" and "C" 517 (region of interest) via a data visualization module, such as a software module, that translates the predefined rectangular region of interest of the test strip 502 into a simulated representation that is displayed on the screen. This simulated representation is referred to as an "image schematic" showing the relative RGB pixel density of one or more test regions normalized to one or more control regions of the same size against a constant color background. Determining the relative pixel density of the "T" and "C" 517 region is called "mobile image ratiometry" and it is applied to the quantitative image analysis of lateral flow immunodiagnostic tests. The image schematic enables the agent (human, robot) imaging the specimen to compare the mobile device/tablet simulation of the test strip 502 to visual inspection to assure that the algorithms are functioning properly and the test strip 502 is oriented in the correct position. The image schematic information may also be transformed into an audio, tactile, or voltage signal to represent the relative Test/Control ratio. The digital image schematic contains all the information needed for ratiometric analysis yet its file size is a small fraction of the original specimen image region of interest. Certain benefits include greater storage capacity, faster data transmission to central or distributed servers and reduces processor activity.

Human perceptual validation of the image schematic simulated representation of the relative ratio of the "T" and "C" 517 regions of an image may be accomplished by showing individuals (humans/onlookers) a test strip 502 or its image on the mobile device or computer display, then allowing them to compare and score it to the image schematic along with other image schematics that deviate from the calculated ratios. Embodiments contemplate individuals being shown two or more images on a screen and asked to choose (rate) between two images according to the Test/Control "T" and "C" region ratio. Using this "game-like" method the Test/Control ratio is not measured absolutely; it is inferred from the collective binary (higher or lower) judgments of the human raters. The rank order of any given image depends on the ratings of the other images and is described mathematically by the Elo formula (see below) for ranking two opponents in a competitor vs competitor match For image A the formula is:

$$E_a = \frac{1}{1 + 10^{\frac{R_b - R_a}{400}}}$$

For image B the formula is:

$$E_b = \frac{1}{1+10^{\frac{R_a-R_b}{400}}}$$

$E_x$ is the expected probability that X will win the match, i.e. $E_a+E_b=1$.
$R_x$ is the rating of X, which changes after every match, according to the formula $(R_x)_n=(R_x)_{n-1}+32\ (W-E_x)$ where W=1 if X wins and W=0 if X loses.
Every image starts with an $R_x=1400$.

In this example, an image score is generally not obtained until it has been matched to at least 10% of the total pool of images that it could be matched against if the image pool size is fixed; otherwise a score is obtained after 100 (or some substantial number) randomly selected from match pairings of an arbitrary sized pool. The results of the scored images may then be used to quantify the images by placing into the image rating pool known or predetermined image ratios as standards. The standards may be derived from Test/Control ratios that have been measured using the modular specimen imaging chamber described above attached to a mobile device or may be simulated by a computer or mobile device as image schematics. This method of human perceptual validation of images may be used in the diagnostics field for quantifying colorimetric or immunobased lateral flow tests that have Test and Control regions.

The composite ratio for ratiometric measurement of Test and Control regions to quantify image pixel density. The composite ratio can be calculated as the weighted average of the test and control regions peak pixel density and the test and control regions areas under the curve. The formula is as follows $(T_{(peak)}/C_{(peak)})/2+(C_{(area)}/C_{(area)})/2$=Composite ratio at 50/50 Peak and Area. Note that other weights can be assigned by changing the denominator. The use of different weighting schemes may be used depending on the type of specimen analysis that is needed.

The composite ratio reduces the image-to-image variability arising from test or control regions of interest that are not homogenous in the pixel density. Subregions of the test or control regions of interest that have very high peaks are seen as dark bands or spot within the regions of interest and these high peaks can produce error and variability when measuring between specimens. To reduce the possibility for error and variability the baseline-subtracted area under the curve within the test and control regions is measured. A curve (created by nonlinear regression) is a series of connected XY points. The software algorithms running on the mobile device use the following trapezoidal integration formula, $\Delta X^*(Y1+Y2)/2$ repeatedly for each adjacent pair of points defining the curve. The area is the result of this calculation and establishes the basis for the $T_{(area)}/C_{(area)}$ ratio. To further reduce image-to-image variability and enhance sensitivity the composite ratio is calculated for three separate images and the results are averaged to produce the final composite ratio.

Embodiments for baseline subtraction method for determining the composite ratio for quantitative ratiometric image analysis contemplated can be used to remove or reduce noise and other artifacts from test and control regions-of-interest of specimen images. The defined rectangular region of interest is determined by the placement of the specimen in the illumination chamber top stage module that is positioned in front of the camera. Embodiments contemplate the RGB values from 0 to 255 measured by the mobile device camera hardware and software for each pixel in the vertical (Y dimension) or horizontal (X dimension). The two-dimensional planar region of interest can then be transformed into a one-dimensional line with a horizontal or vertical orientation. This dimensional transformation is termed a line profile and it establishes the basis for all subsequent quantitative measurements of the region of interest. The first point of the horizontal or vertical line profile is used to establish the starting baseline. The middle point of the line profile is used as a second point to establish the baseline. The last point in the line profile is used as the third point to establish the baseline. A line curve is fit between the first and second points and again between the second and third points. These two curve fits are merged into one curve fit, which is then subtracted from the region of interest line profile. This procedure establishes the baseline pixel as zero and it de-trends the line profile by removing background shadows or noise. The resultant baseline subtracted line profile is the dataset that is used for peak and area calculations and provides the information needed to create the composite ratio and the image schematic.

An alternative method to remove the initial baseline value from the line profile is envisioned to be to establish the line profile as described above and then differentiate the line by calculating the point-to-point slope change to produce a slope line profile, then integrating the slope line profile using point-to-point trapezoidal integration ($\Delta X^*(Y1+Y2)/2$). The original shape of the line profile is re-established with the baseline offset removed. This technique removes the initial baseline, but generally will not remove background noise or shadows across the line profile.

An alternative method to remove the initial baseline value from the line profile envisioned to be to calculate the central tendency (average, median or mode) of a range of values in the beginning of the line profile before the signal begins and subtract the average, median or mode value from the entire line profile and determine which of the three produces the largest signal-to-noise ratio or most reliable result across several images. Under most circumstances when the baseline noise is normally distributed the average is approaching optimal. Under conditions where there are large transient artifacts in the baseline segment of the line profile the median would yield reasonable results.

Figure 7:
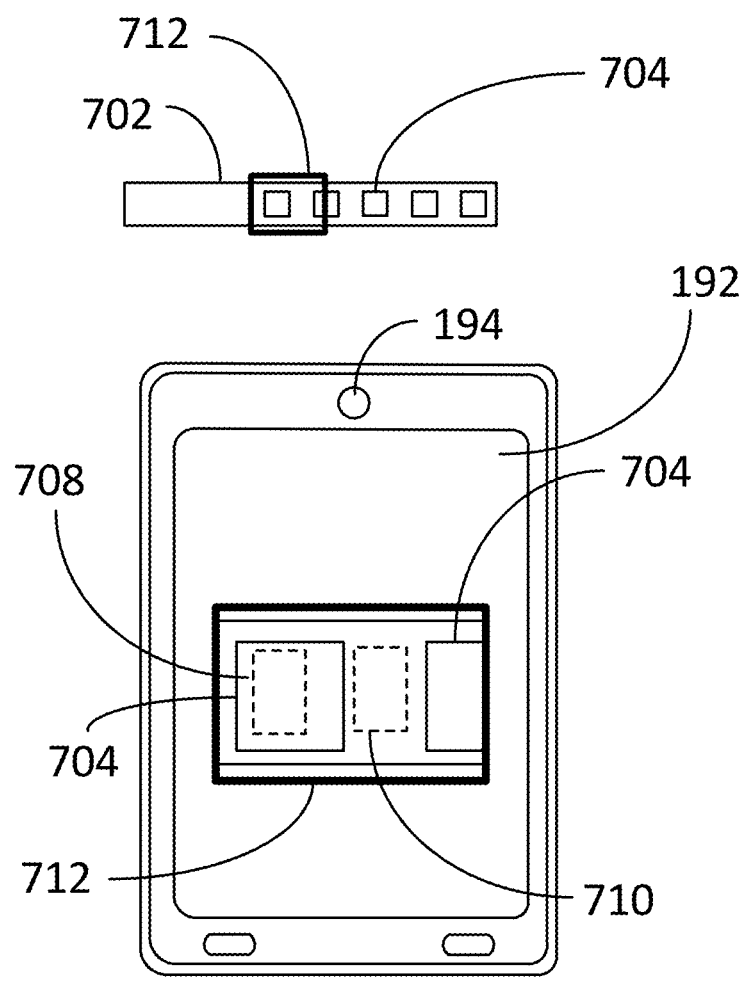
FIG. 7 illustratively depicts a test strip embodiment with an image schematic of a region of interest within an image displayed on a screen consistent with embodiments of the present invention.

An example where certain embodiments of the present invention can be commercially practiced is illustratively shown in FIG. 7. FIG. 7 shows the colorimetric quantification of a colorimetric test with five colored changing pads 704. The test strip 702 is placed in the illumination chamber 102, illuminated with the display screen 192, and imaged via the front facing camera 194 (the image is the darkened rectangle 712 indicating the boundary of the picture frame). The resulting image 712 is shown on the display screen 192. The region of interest is defined by the person operating the mobile phone/tablet 190 by drawing a single box around the signal 708 and background 710 of the sample image 712. The signal box 708 and background box 710 are equal sized boxes. The average Red, Green, Blue (RGB) color channel values are determined for the two boxes 708 and 710 and the ratio of the signal/background is compared to known standards for each colored pad of interest.

Certain embodiments contemplate the data visualization module being a software program running on the tablet/phone 190 that translates a predefined rectangular region of interest, which positions itself over the picture 712 (box 708 and 710, for example) of the test strip 702 that is displayed on the display screen 192. The region of interest is determined by the correct positioning of the test strip/specimen 702 within the image illumination chamber 102 and over the front facing camera 194.

Figure 8:
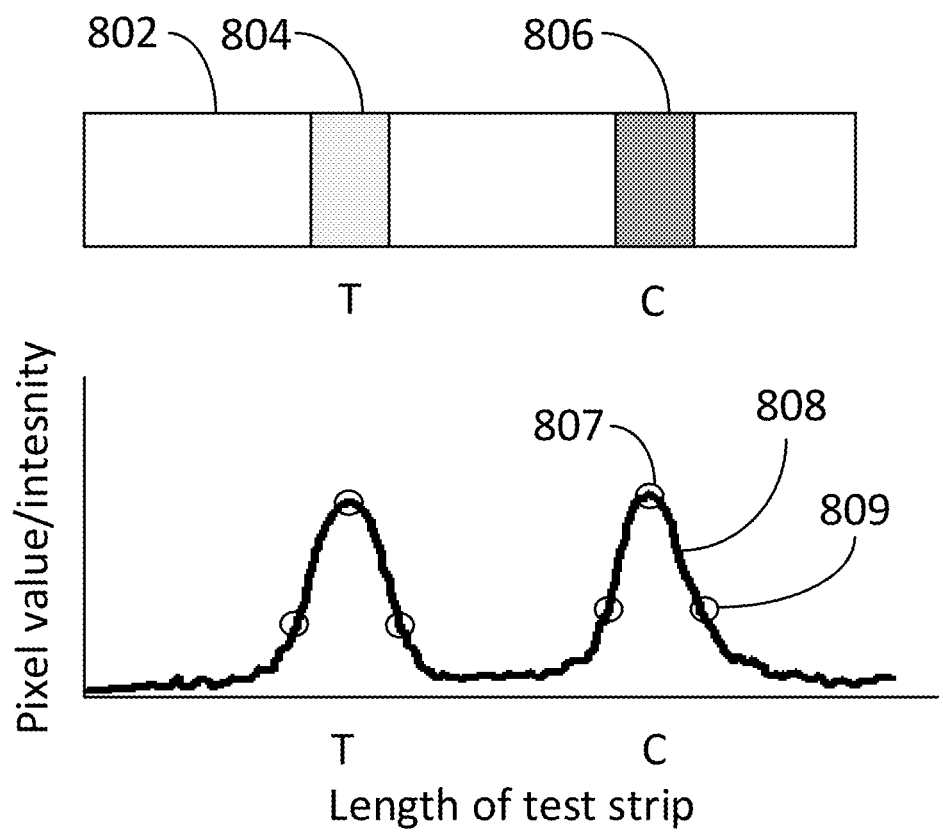
FIG. 8 depicts an image schematic representation of normalized RGB pixel values of a Test and Control image taken from a test strip image baseline determination consistent with embodiments of the present invention.

FIG. 8 depicts an Image Schematic representation of normalized RGB pixel values of a Test and Control image taken from a test strip image. Here, a sample material is applied to a test strip 802, which after some time becomes developed revealing the "T" and "C" lines 804 and 806. The graph 808 represents the relative RGB pixel density of the test region 804 and the control region 806. In the graph, test region 804 is normalized to the control region 806 against a constant color background. The Peak-Baseline, wherein the peak 807 and the baseline 809 are depicted with circles on the graph iterate, for the control band 806 and test band 804 are calculated and expressed as it Peak Ratio. The Area under the curve is measured for each test band 804 and control band 806 defined from peak to right and left baseline points expressed as the Area Ratio. The 50/50 waiting of the Test Ratio and the Area Ratios to find the Composite Ratio, which is used for the image schematic and comparison to a standard curve.

Figure 9:
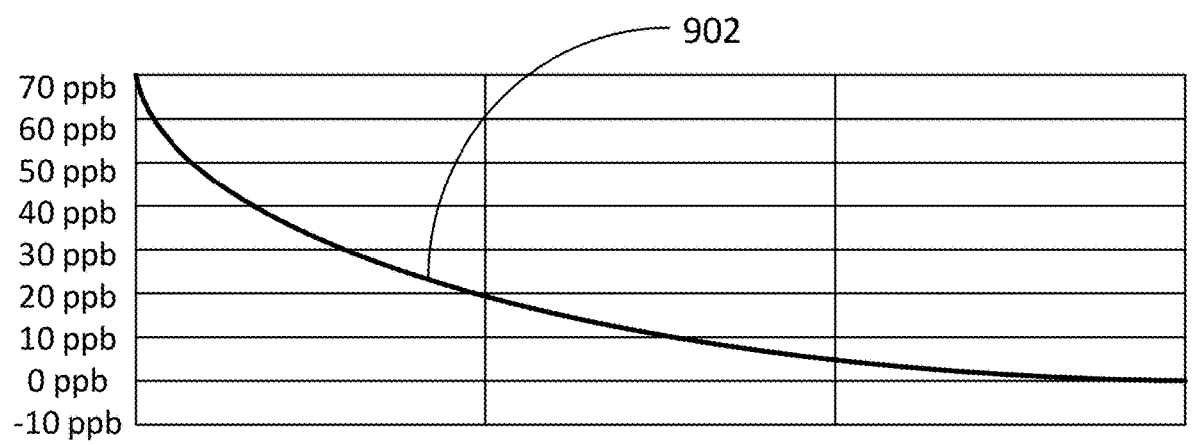
FIG. 9 depicts an example of identifying concentration of a substance by way of fitting a test result on the known curve consistent with embodiments of the present invention.

FIG. 9 depicts an example of identifying concentration of a substance in parts per billion (ppb) by way of fitting a test result on the known curve. In this example, "T" and "C" ratios are obtained for a peanut aflatoxin 2 band lateral flow test. For this test, an image score is generally not obtained until it has been to at least 10% of the total pool of damages that it could be matched against if the image pool size is fixed; otherwise the scores obtained after 100 (or some other substantial number) randomly selected from match pairings of arbitrary sized pool. The results of the scored images may then be used to quantify images by curve fitting and interpolation or predetermined image ratios as standards. The standards may be derived from Test/Control ratios that have been using the modular specimen imaging chamber 102. Once the Test/Control ratio is obtained, it is placed on the appropriate calibration curve (e.g. 100% equals 18 ppb—parts per billion). The standard curve is generated from known standards of multiple calibrations. The results obtained from the imaging notify users of amount that quantifies the analyte.

An alternative method for baseline subtraction, de-trending and background subtraction from a line profile can be accomplished by differentiating the line profile as described above to generate the slope line profile, then transforming the slope line profile by calculating the absolute slope values and replacing the negative slope values with the absolute values. This absolute slope line profile transformation effectively removes background from the line profile. The Test and Control peaks and areas may then be determined and used for the composite ratio calculation.

Embodiments for baseline subtraction method for determining the Composite ratio for quantitative ratiometric image analysis contemplated are used to remove or reduce noise and other artifacts from test and control regions-of-interest of specimen images 712. The defined rectangular region of interest 708 is determined by the placement of the specimen 702 in the illumination chamber top stage module 102 that is positioned in front of the camera 194. Embodiments contemplate the RGB values from 0 to 255 measured by the mobile device camera 194, hardware and software for each pixel in the vertical (Y dimension) or horizontal (X dimension). The two-dimensional planar region of interest can then be transformed into a one-dimensional line with a horizontal or vertical orientation. This dimensional transformation is called a line profile and it establishes the basis for all subsequent quantitative measurements of the region of interest. The first point of the horizontal or vertical line profile is used to establish the starting baseline. The middle point of the line profile is used as a second point to establish the baseline. The last point in the line profile is used as the third point to establish the baseline. A line curve is fit between the first and second points and again between the second and third points. These two curve fits are merged into one curve fit, which is then subtracted from the region of interest line profile. This procedure establishes the baseline pixel as zero and it de-trends the line profile by removing background shadows or noise. The resultant baseline subtracted line profile is the dataset that is used for peak and area.

Figure 10A:
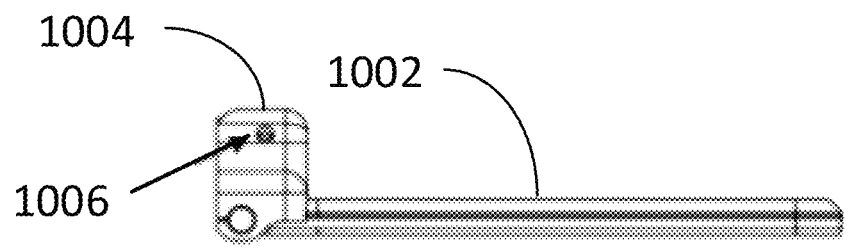
FIGS. 10A-D depicts an optional embodiment of a system for testing colored solutions containing DNA or color indicators in liquid form consistent with embodiments of the present invention.
Figure 10B:
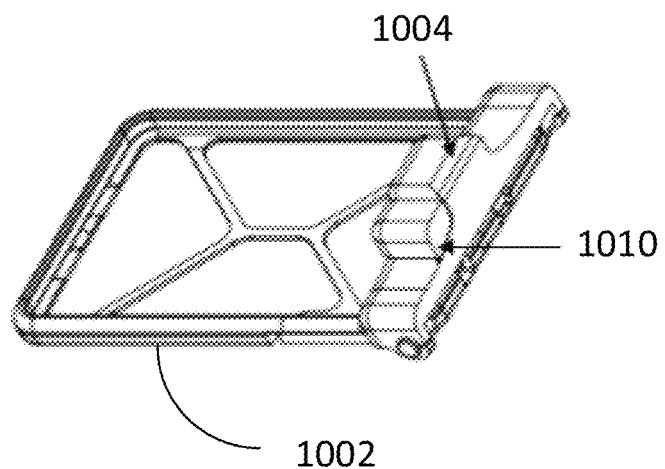
Figure 10C:
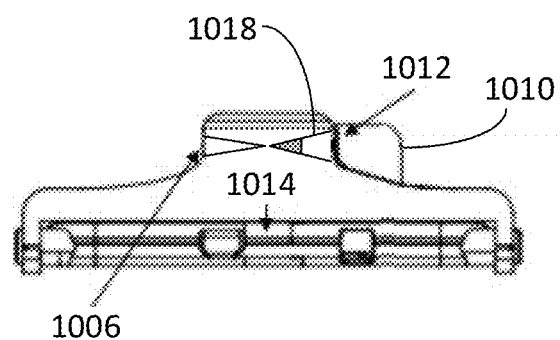
Figure 10D:
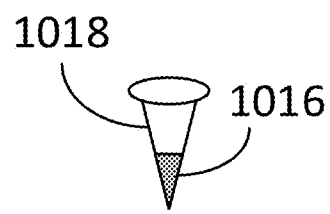

FIG. 10A depicts an optional embodiment to test colored solutions containing DNA or color indicators in liquid form consistent with embodiments of the present invention. As shown, the protective case/tablet holder 1002 is similar to that shown in FIG. 1, however the hood and chamber 1004 possess an external light source 1006. FIG. 10B depicts a different view of the protective case/tablet holder 1002 possesses a sample tube and light cover 1010. FIG. 10C shows the hood in chamber 1004 with a cone shaped liquid sample in a plastic tube 1018 disposed in an accommodating opening in the chamber 1012 and the external light source 1006. For reference, there is a lens 1014 that brings the sample 1016 into focus either by changing the focal length of the forward facing camera 194 and/or magnification of the sample 1016. FIG. 10D depicts a cone shaped plastic tube 1018 containing a liquid sample 1016. One embodiment contemplates the external light being produced by an LED in specific wavelengths such as ultraviolet, or some other specific wavelength in or outside the visual light spectrum. Unlike the other illumination chamber depicted in FIGS. 1-6, illumination chamber of FIG. 10A-D uses an external light, such as an LED, instead of the touch screen 192 to illuminate the sample 1016. As shown in this embodiment, there is a hole for an external light source 1016, such as an LED of any wavelength is abutted against the clear to with 10-100 microliters of liquid contained in the cone shaped plastic tube 1018. The sample is illuminated and the color is measured using the RGB color planes in the image from the front facing camera 194 on the tablet or phone 190. From the image, the RGB values can be quantified for the region of interest of the solution and compared to known standards for the analyte being measured. This can be applied for DNA amplification measurement when combined with a DNA indicating dye. It can also be used to quantify proteins in a solution when combined with the appropriate dyes.

Figure 11:
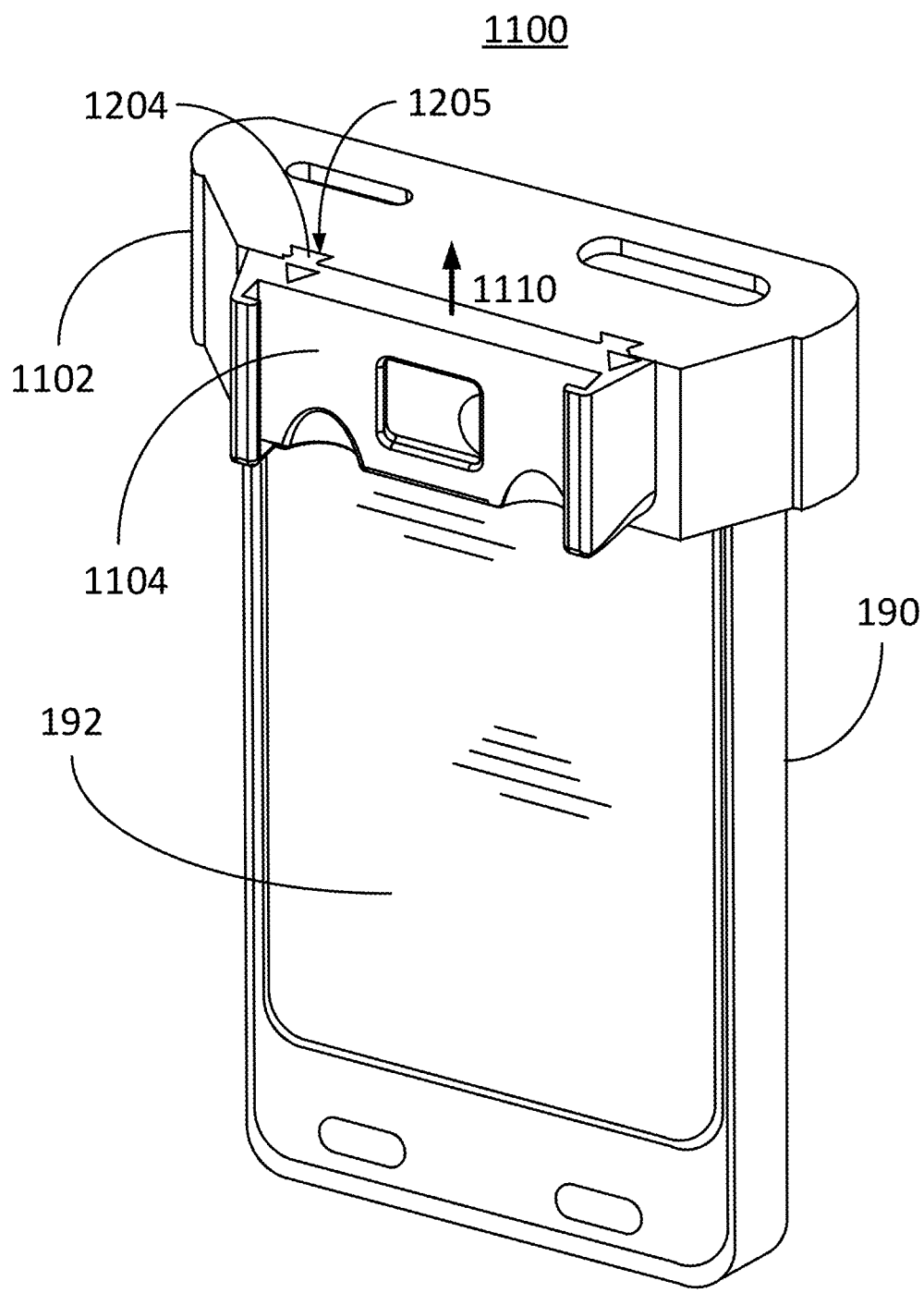
FIG. 11 depicts an optional embodiment of an illumination chamber in a cooperating relationship with a hand held electronic device consistent with embodiments of the present invention.

FIG. 11 illustratively depicts another embodiment of an illumination chamber cooperating with a personal electronic device, such as a smartphone or tablet, consistent with embodiments of the present invention. As shown, a slide-on hood 1102 is covering the top of the smartphone/tablet 190. The illumination chamber is configured to attenuate a significant portion of ambient light sources originating outside of the electronic smartphone/tablet 190. Certain embodiments of the slide-on hood 1102 comprise the functionality of the hood 110, however the slide-on hood 1102 is not pivoted over the smartphone/tablet 190, rather is slid over the top of the smartphone/tablet 190 positioned at essentially in the same location as the hood 110 relative to the smartphone/tablet 190 of FIG. 1. In the present figure, the slide-on hood 1102 covers a portion of the screen 192 to collect light emitted by the screen 192 from the tablet 190 in the same way as the hood 110. Certain embodiments contemplate the portion of the screen 192 covered by the slide-on hood 1102 is in the range between 1% to 20% of the screen. Other embodiments envision a portion of the screen 192 covered by the slide-on hood 1102 is less than 50% screen 192 and yet others is less than 30% of the screen 192. Other embodiments envision utilizing less than an amount of light produced by the entire screen 192. Certain other embodiments envision the illumination chamber covering the entire surface of the screen 192.

Also depicted here is yet another embodiment of the top chamber 1104 connected to the slide-on hood 1102 by way of a pair of locking wedges 1204 that slidingly mate with wedge shaped channels 1205 in the slide hood 1102 (dovetail tongue and groove). The wedge shaped channels 1205 are sized to receive the wedges 1204. When the locking wedges 1204 are engaged with the wedge shaped channel 1205, the top chamber 1104 is locked in place except for being removed via the direction of the arrow 1110. Certain embodiments envision the wedge shaped channels 1205 and/or the locking wedges 1204 being sized to fit snugly together. Further embodiments contemplate a material, such as rubber, that essentially fixedly retains the top chamber 1104 to the slide to the hood 1102 via friction between the wedge shaped channels 1205 in the locking wedges 1204. Essentially fixedly retained as used herein is intended to mean that the top chamber 1104 will stay attached to and in imposition on the hood 1102 unless manipulated intentionally to be separated. Certain embodiments contemplate other techniques for removably connecting the top chamber 1104 to the slide-on hood 1102, such as one or more pegs and accommodating holes, magnets, snaps, etc. Certain of these examples may be improved with material choice, such as a rubber lined hole that "grabs" a peg, thus essentially fixedly holding the top chamber 1104 to the slide-on hood 1102 that can be separated by manually pulling apart, for example.

Figure 12A:
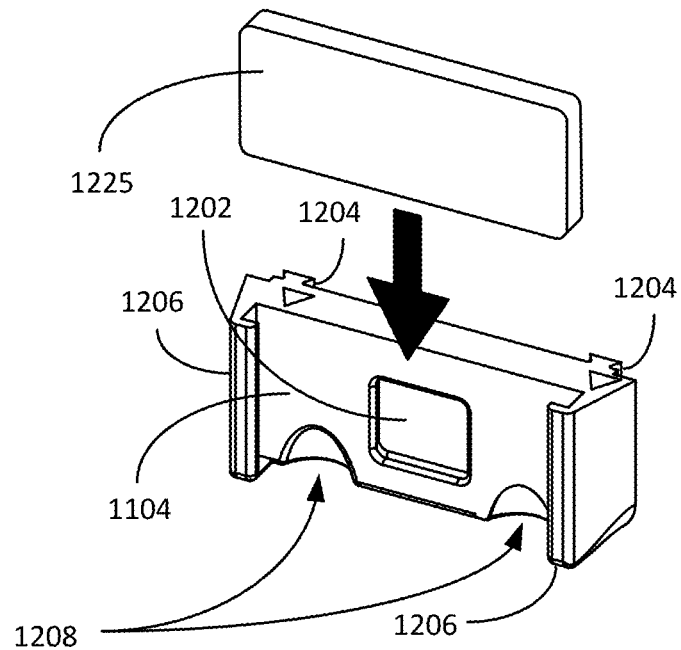
FIGS. 12A and 12B depict top chamber and test device holder consistent with embodiments of the present invention.

FIG. 12A illustratively depicts an embodiment of the top chamber 1104 consistent with embodiments of the present invention. In greater detail, the top chamber 1104 shows the pair of locking wedges 1204 adapted to slidingly engage with mating wedge recesses 1205 in the slide-on hood 1102 (see FIG. 11). The top chamber 1104 further provides a top chamber aperture 1202 that receives light collected from a portion of the screen 192 by the slide-on hood 1102. The top chamber 1104 is adapted to receive and hold a test device holder 1225, adapted to hold the test strip 502 or some other related test device within the scope and spirit of the present invention, in place via a pair of retaining brackets 1206 sized to make a channel that accommodate the test device holder 1225. Certain embodiments envision the retaining brackets 1206 sized to snugly fit the test device holder 1225 so that the test device holder 1225 is retained in position in the top chamber 1104 by friction. The top chamber 1104 further possesses a pair of finger recesses 1208 whereby a human can easily push the test device holder 1225 from the top chamber 1104 with their fingers via the finger recesses 1208.

Figure 12B:
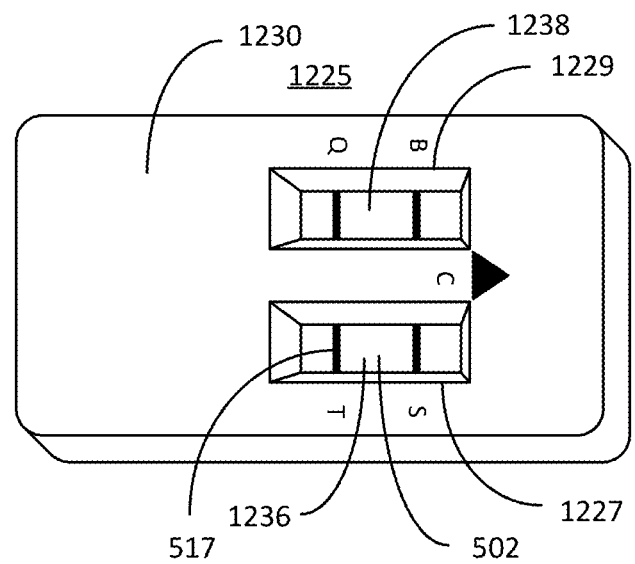

FIG. 12B illustratively depicts an embodiment of the test device holder system with embodiments of the present invention. As shown, this test device holder 1225 provides room for two test device 1236 and 1238 that are exposed through the first test device window 1227 and the second test device window 1229, respectively. The test device windows 1227 and 1229 are configured and arranged to be seen by the camera lens 194 (a camera in a smartphone/tablet 190 is typically comprised of a camera-on-a-chip, which can be a CMOS active pixel sensor and associated software and circuitry known to those skilled in the art) and illuminated from light produced by the screen 192 via the top chamber aperture 1202 when positioned with the test device window facing surface 1230 adjacent to (face to face) with the top chamber aperture 1202. In other words, when arranged as shown, the two test device 1236 and 1238 can be exposed to the light from the screen 192 and read by the camera 194. Importantly, test device windows 1227 and 1229 receive light from the screen through the top chamber aperture 1202 when engaged with the top chamber 1104.

Figure 13A:
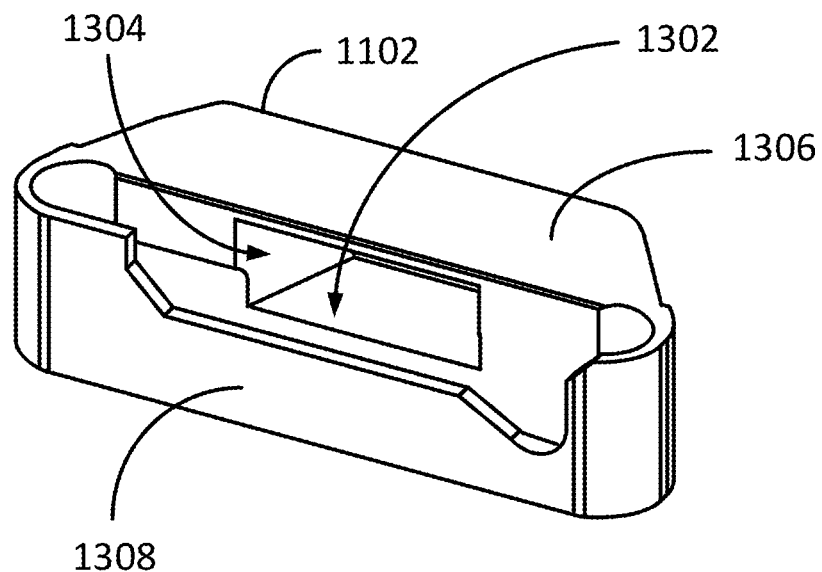
FIGS. 13A and 13B illustratively depict different views of a slide-on hood embodiment consistent with embodiments of the present invention.
Figure 13B:
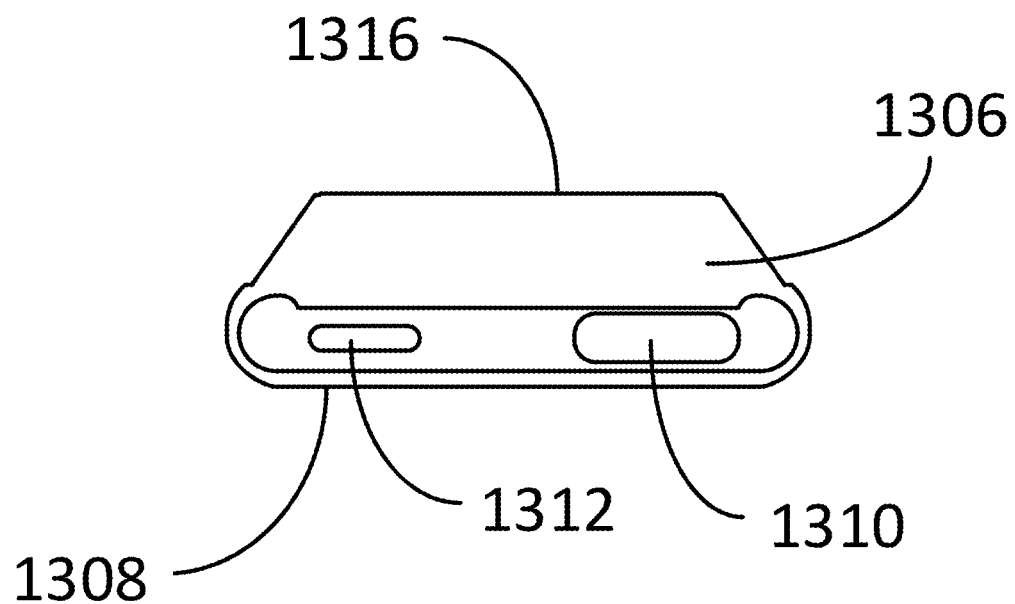

FIGS. 13A and 13B illustratively depict different views of a slide-on hood embodiment consistent with embodiments of the present invention. FIG. 13A shows perspective view of the slide-on hood 1102 with the slide-on hood base 1308 shown for reference. The top of the smartphone/tablet 190 slides into, or otherwise engages, the smartphone/tablet space 1302. The slide-on hood 1102 collects light from a portion of the screen 192 and channels that light to illuminate the test device, which in one embodiment is a test strip 502, that are exposed through the test device windows 1227 and 1229 via slide-on hood aperture 1304. The slide-on hood opening 304 also provides an unobstructed line of sight between the camera 194 and the test device 502. In this way, the camera and lens system 194 are therefore adapted to capture an image of the illuminated test device with the camera and lens system 194 in real-time while the test device 502 is developing or after the test device 502 is developed. The camera-captured image of the test device can be post processed to analyze the result of a developing or developed test device 502. Certain embodiments contemplate the slide-on hood 1102 matingly engaging the smartphone/tablet 190 in a tightly conforming relationship. Some embodiments further envision the slide-on hood 1102 being retained position on the smartphone/tablet 190 by way of friction, possibly through material choice such as rubber. The front surface 306 is shown here for reference.

FIG. 13B shows a front surface view of the slide-on hood 1102. Also shown for reference are the slide-on hood base 1308 and the slide-on hood top 1316. Inside the smartphone/tablet space 1302 are a first access port 1310 and a second access port 1312 that provide an opening to access power or control buttons on the smartphone/tablet 190. Certain embodiments envision no access ports, while other embodiments envision one or more access ports having a different shape and/or different locations in the slide-on hood 1102.

Figure 13C:
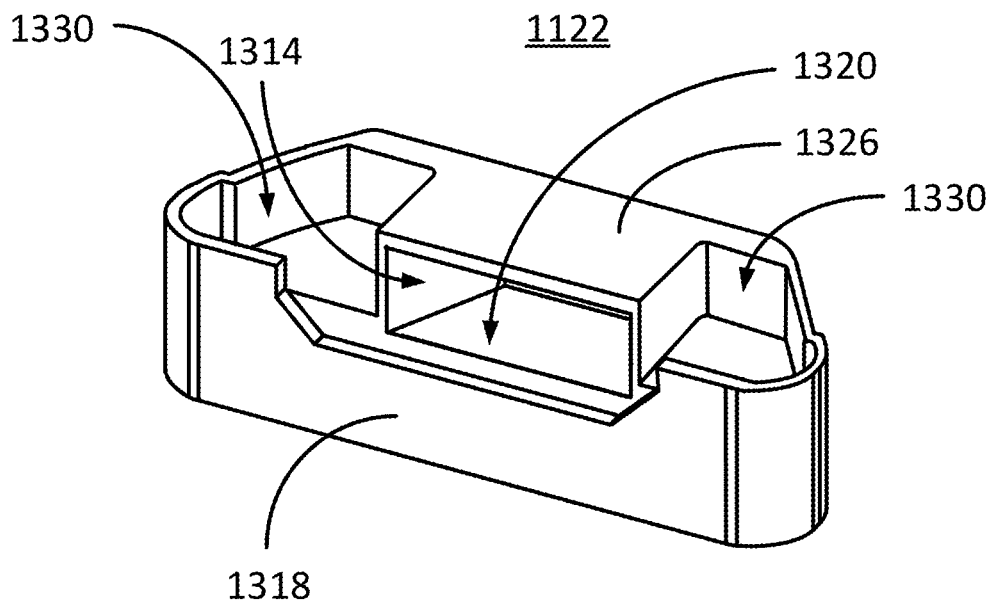
FIGS. 13C and 13D illustratively depict views of an optional slide-on hood embodiment consistent with embodiments of the present invention.
Figure 13D:
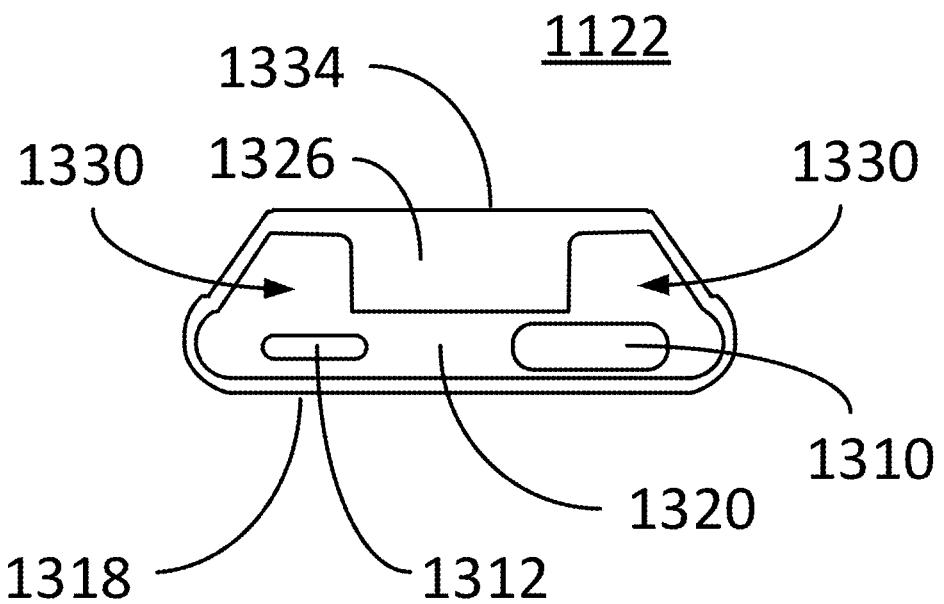

FIGS. 13C and 13D illustratively depict views of a different slide-on hood embodiment from the embodiment of FIGS. 13A and 13B consistent with embodiments of the present invention. FIG. 13C shows a perspective view of the slide-on hood 1122. For reference, the slide-on base 1318 and front surface 1326 are visually displayed. The top of the smartphone/tablet 190 slides into, or otherwise engages, the smartphone/tablet space 1320. The slide-on hood 1122 collects light from a portion of the illuminated screen 192 to illuminate the test device 502 that are exposed through the test device windows 1227 and 1229 via the slide-on hood opening 1314. The slide-on hood opening 1314 provides an unobstructed line of sight between the camera 194 and the test device 502 (sample) when the illumination chamber overlays the lens/camera system 194. Certain embodiments contemplate the slide-on hood 1122 engaging the smartphone/tablet 190 in a tightly conforming relationship that can be held in place by friction requiring manipulation to separate the smartphone/tablet 190 from the slide-on hood 1122. Finally, the slide-on hood 1122 shows a pair of fingertip recesses 1330, which are each adapted to accommodate a human finger to assist in prying apart the slide-on hood 1122 from the smartphone/tablet 190 (when they are engaged).

FIG. 13D shows a front surface view of the slide on hood 1122. For reference, the slide-on base and front surface 1326 are visually displayed. Inside the smartphone/tablet space 1302 are a first access port 1310 and a second access port 1312. The finger recesses 1330 are also shown.

Figure 14:
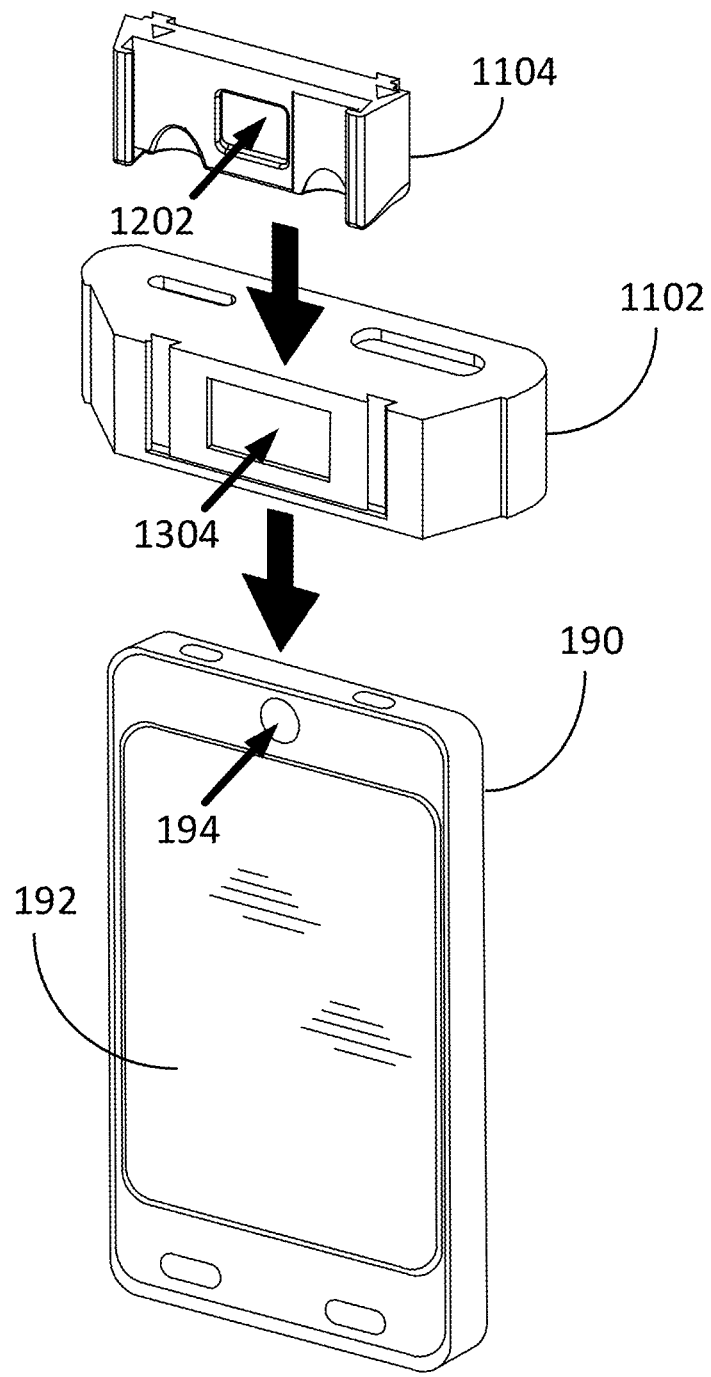
FIG. 14 illustratively depicts an exploded view of the illumination chamber system as shown in FIG. 11 consistent with embodiments of the present invention.

FIG. 14 illustratively depicts an exploded view of the illumination chamber system as shown in FIG. 11 consistent with embodiments of the present invention. As shown here, the top chamber 1104 slides onto the slide-on hood 1102 via the locking wedges 1204 and the wedge shaped channels 1205 system. The slide-on hood 1102 slides over the smartphone/tablet 190 shown by the arrows. When engaged, light from the screen 192 is collected by the slide-on hood and is channeled through the slide-on hood aperture 1304 and the top chamber aperture 1202 to the test device (not shown). The test device holder 1225 is not shown in the interest of space, but is appropriately shown in FIG. 12A with an arrow consistent with that of FIG. 14. Also as can be readily seen here, the camera lens 194 has clear visibility to the test device (not shown) by way of the slide-on hood aperture 1304 and the top chamber aperture 1202. In other words, the top chamber aperture 1202 and the slide-on hood aperture 1304 when fit together properly provide a pathway (which in one embodiment is unobstructed) between the camera lens 194 and the test device 502. The illumination chamber system adapted to bias the light source via the pathway to favor collected light originating from the illuminating screen 192 to the test device 502 while concomitantly attenuating the ambient light sources originating outside of the light pathway between the lit screen 192 and the test device 502, the pathway also configured to provide the camera and lens system 194 with a view of the test device 502. Certain embodiments envision the slide-on hood 1102 and the top chamber 1104 shielding the test device 502 from non-screen (meaning other than the illuminating screen 192) derived ambient light when installed over the smartphone/tablet 190. In certain embodiments, the slide on hood 1102 and the top chamber 1104 shield a "significant portion" of screen-reflected ambient light from the device holder slots 1504 is considered less than 25% illumination from screen-reflected ambient light and at least 75% illumination directly from the lit screen 192. Certain other embodiments contemplate eliminating any direct light source other than the illumination from the lit screen 192 and whatever screen-reflected ambient light not blocked by the slide on hood 1102. Yet some embodiments envision the illumination of the test device 502 being predefined whereby the intensity of the illuminating screen 192 is adjusted (either manually or automatically) to compensate for screen-reflected ambient light that may contribute to illuminating the test device region of interest 502.

Certain embodiments envision light wavelength and intensity being filtered and/or adjusted by way of the microprocessor/s in the smartphone/tablet 190 to provide flexibility around the light spectrum and time of exposure for purposes of optically measuring a test device region of interest 502 (influencing the reaction process in the test regions 502). Certain embodiments envision the light wavelength and intensity being filtered and/or adjusted in the smartphone/tablet screen192 to provide the camera 194 and adequate "light" signal to read the test regions 502. While other certain embodiments envision an external lens or light spectral bandpass filter interposed between the camera lens 194 and the test region 502, whereby in one example the lens (not shown) or filter is integrated in the slide-on hood 1102. Other embodiments contemplate the camera lens 194 requiring no external lens in order to adequately measure the test device region of interest 502.

Figure 15A:
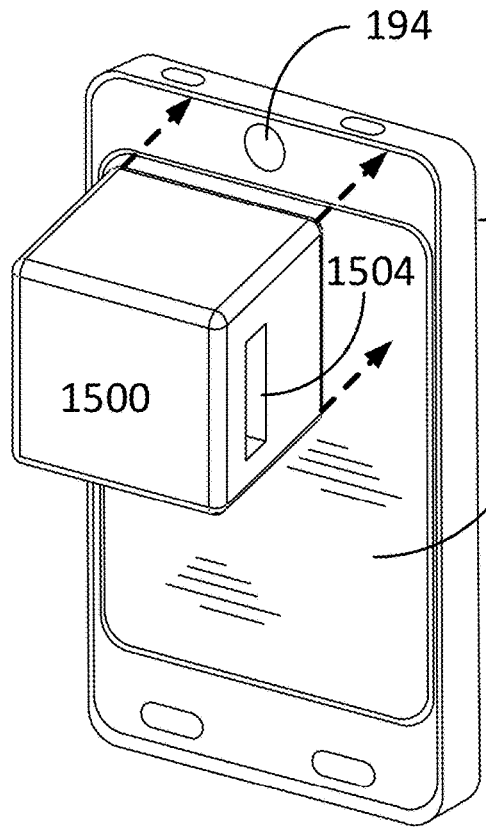
FIGS. 15A, 15B and 15C illustratively depict another illumination chamber embodiment consistent with embodiment of the present invention.
Figure 15B:
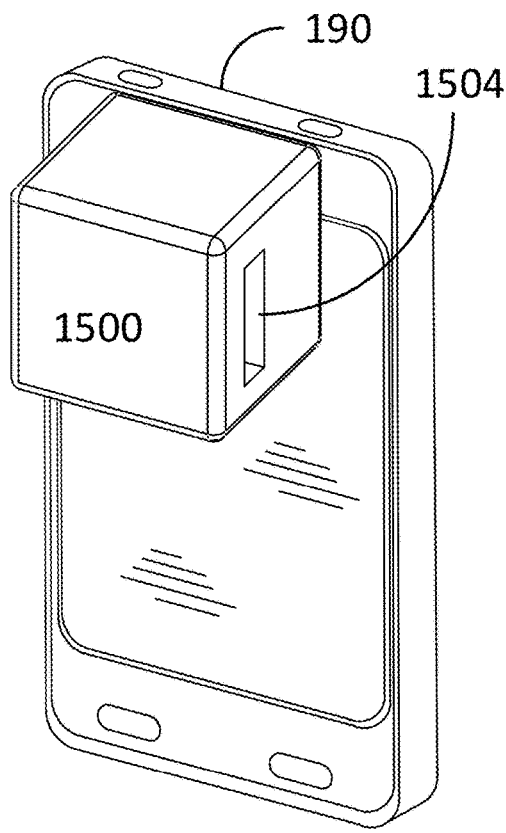
Figure 15C:
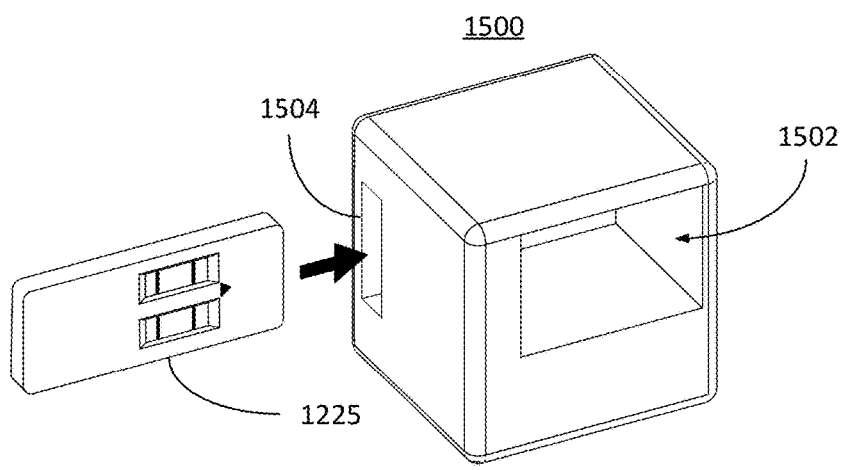

FIGS. 15A, 15B and 15C illustratively depict another illumination chamber embodiment consistent with embodiment of the present invention. As shown in FIG. 15A, the standalone illumination chamber 1500 provides the flexibility of being used with a variety of different smartphones/tablets or other devices possessing a screen and camera that can be used consistently within the scope and spirit of the present invention. The three 'dashed' arrows indicate where the standalone illumination chamber 1500 will be placed on the smartphone/tablet 190. Consistent with other embodiments the present invention, the standalone illumination chamber 1500 placed above the camera lens 194 and a portion of the screen 192. FIG. 15C illustratively depicts the other side of the standalone illumination chamber 1500 consistent with embodiments of the present invention. The test device holder 1225 as shown by an arrow is adapted to be inserted into the standalone illumination chamber 1500 through the test device holder slot 1504. A standalone illumination chamber aperture 1502 is configured and arranged to asymmetrically overlay the camera lens 194 and a portion of the screen 192 while essentially shielding the test device 502 from ambient light (external to the smartphone/tablet 190). Accordingly, the standalone illumination chamber asymmetrically positioned aperture 1502 is configured and adapted to specifically collect light from the screen 192 and provide an unobstructed camera image view of the test device region of interest 502 in the camera 194 in only one of two possible 180 degree horizontal planar orientations. 15B illustratively shows the standalone illumination chamber 1500 resting atop the smartphone/tablet 190. Certain embodiments envision the standalone illumination chamber 1500 being manually placed over the camera 194 and a portion of the screen 192 and either manually held in place or resting in position by way of gravity. Certain other embodiments envision the standalone illumination chamber 150 of being held in place by a strap, rubber band, or universal fixture.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe a protective case for use with a tablet or cell phone, it is contemplated that other similar devices can be used for biological testing within the scope and spirit of the present invention can be used while still maintaining substantially the same functionality without departing from the scope and spirit of the present invention. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A test sample apparatus operably used with a handheld electronic device, the handheld electronic device possessing a front surface having an illuminating screen and a camera, the handheld electronic device further possessing a top, two sides and a bottom, the camera lens is closer to the top than the bottom, the test sample apparatus comprising:
an illumination chamber adapted to cover a portion less than the entirety of the illuminating screen, the illumination chamber configured to overlay a camera lens, the illumination chamber further configured to collect light from the illuminating screen while the illuminating screen is activated, the illumination chamber configured to attenuate a significant portion of ambient light sources originating outside of the electronic device, the illumination chamber possessing a slot adapted to receive the top of the handheld electronic device in a sliding relationship;
a top chamber integrated with the illumination chamber, the top chamber providing a test device holder slot adapted to accommodate a test device holder, the test device holder arranged to hold a test device, the illumination chamber and the top chamber collectively provide a pathway configured to bias the light source to favor collected light originating from the illuminating screen to the test device while concomitantly attenuating the ambient light sources originating outside of the light path between the illuminating screen and the test device, the pathway also configured to provide the camera with a view of the test device.

2. The test sample apparatus of claim 1 wherein the pathway from the camera lens and screen to the test device is unobstructed.

3. The test sample apparatus of claim 1 wherein the portion is less than 30% of the illuminating screen.

4. The test sample apparatus of claim 1 wherein the illumination chamber and the top chamber shield at least 75% of the ambient light, which is nonscreen-derived, from reaching the device holder slot when the illumination chamber and top chamber is engaged with the handheld electronic device.

5. The test sample apparatus of claim 4 wherein the only light source provided to the test device, other than the screen-reflected ambient light, is from the illuminating screen.

6. The test sample apparatus of claim 1 wherein the test sample apparatus is a slide-on hood adapted to slide over the top of the handheld electronic device in a conforming relationship.

7. The test sample apparatus of claim 1 wherein the top chamber integrates with the illumination chamber by way of a locking mechanism.

8. The test sample apparatus of claim 7 wherein the locking mechanism is a wedge and channel system frictionally held in place, peg and hole arrangement, magnets, or snaps.

9. A method comprising:
providing a handheld electronic device possessing a front surface having an illuminating screen and a camera;
placing a test device in a chamber integrated with a light collecting hood, the light collecting hood adapted to significantly block ambient light originating from other than the illuminating screen;
positioning the light collecting hood over the camera and a portion of the illuminating screen that when positioned inherently provides a pathway between the camera and the test device;
illuminating the test device from light produced by illuminating the screen;
capturing an image of the illuminated test device with the camera in real-time while the test device is developing or after the test device is developed; and
post processing of the camera-captured image of the test device.

10. The method of claim 9 further comprising developing the test device and imaging the test device under a specific spectral band of visible light generated by the illuminating screen.

11. The method of claim 10 further comprising sliding the illuminated screen light collecting hood over a portion of the handheld electronic device prior to the illuminating step.

12. The method of claim 10 further comprising positioning the light collecting hood over a portion of the illuminating screen prior to the illuminating step.

13. A test sample apparatus operably used with a handheld electronic device, the handheld electronic device possessing a front surface having an illuminating screen and a camera, the handheld electronic device further possessing a back surface, a top, two sides and a bottom, the camera is closer to the top than the bottom, the test sample apparatus comprising:
an illumination chamber adapted to cover a portion less than the entirety of the illuminating screen, the illumination chamber configured to overlay the camera lens, the illumination chamber further configured to collect light from the illuminating screen while the illuminating screen is activated;
a top chamber integrated with the illumination chamber, the top chamber providing a test device holder slot adapted to accommodate a test device holder, the test device holder arranged to hold at least one test device, the illumination chamber and the top chamber collectively provide a pathway configured to funnel the collected light from the illuminating screen to the test device, the pathway also configured to provide the camera with a view of the test device.

14. The test sample apparatus of claim 13 wherein the pathway is unobstructed.

15. The test sample apparatus of claim 13 wherein the illumination chamber further possesses a slot adapted to receive the top of the handheld electronic device in a sliding relationship.

16. The test sample apparatus of claim 13 wherein the illumination chamber is figured to be manually held in a position that aligns the camera in view of the test device via the pathway and funnels the collected light from the illuminating screen to the test device.

17. The test sample apparatus of claim 13 wherein the portion is less than 50% of the illuminating screen.

18. The test sample apparatus of claim 13 further comprising a means for attaching the top chamber with the illumination chamber.

19. The test sample apparatus of claim 13 wherein the principle light source provided to the test device is from the screen and less than 25% indirect non-screen generated ambient light.

\* \* \* \* \*